(12) United States Patent
Sharifi et al.

(10) Patent No.: US 8,465,976 B2
(45) Date of Patent: Jun. 18, 2013

(54) METHODS FOR ISOLATING AND USING HEMATOPOIETIC AND EMBRYONIC STEM CELLS OF THE PERITONEAL CAVITY

(75) Inventors: Behrooz Sharifi, Woodland Hills, CA (US); Lai Wang, La Verne, CA (US); Prediman K. Shah, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 354 days.

(21) Appl. No.: 12/526,661

(22) PCT Filed: Feb. 12, 2008

(86) PCT No.: PCT/US2008/053725
§ 371 (c)(1),
(2), (4) Date: Aug. 11, 2009

(87) PCT Pub. No.: WO2008/100936
PCT Pub. Date: Aug. 21, 2008

(65) Prior Publication Data
US 2010/0040585 A1    Feb. 18, 2010

Related U.S. Application Data

(60) Provisional application No. 60/889,442, filed on Feb. 12, 2007.

(51) Int. Cl.
*C12N 5/00* (2006.01)
*C12N 5/071* (2010.01)
*C12N 5/074* (2010.01)

(52) U.S. Cl.
USPC ........... 435/378; 435/325; 435/354; 435/366; 435/395; 424/93.1

(58) Field of Classification Search
None
See application file for complete search history.

(56) References Cited

U.S. PATENT DOCUMENTS

| 5,777,193 | A  * | 7/1998  | Dunn et al. ................ 800/3 |
| 6,227,202 | B1   | 5/2001  | Matapurkar |
| 6,821,513 | B1   | 11/2004 | Fleming |
| 8,071,377 | B2 * | 12/2011 | Bernstein et al. .......... 435/377 |
| 2005/0014255 | A1 * | 1/2005 | Tang et al. ................. 435/366 |
| 2005/0124003 | A1 | 6/2005 | Atala et al. |
| 2005/0232896 | A1 | 10/2005 | Schwarz |
| 2005/0255588 | A1 | 11/2005 | Young et al. |
| 2009/0022777 | A1 | 1/2009 | Mathiowitz et al. |

FOREIGN PATENT DOCUMENTS

| WO | 2005033268 A2 | 4/2005 |
| WO | 2005072341 A2 | 8/2005 |
| WO | 2008100936 A2 | 8/2009 |

OTHER PUBLICATIONS

Harrick et al., Int J Biochem Cell Biol. Apr. 2004;36(4):621-642.*
Campbell et al. Circulation Research, 85:1173-1178, 1999.*
Campbell et al., Journal of Vascular Research, 2000, vol. 37 Issue 5, p. 364-371.*
Osawa et al., Science 273:242-246, 1996.*
PCT/US08/53725 Written Opinion dated Jul. 11, 2008.
PCT/US08/53725 IPRP dated Aug. 19, 2009.

* cited by examiner

*Primary Examiner* — Daniel C Gamett
(74) *Attorney, Agent, or Firm* — Seth D. Levy; Nixon Peabody LLP

(57) ABSTRACT

The invention relates to the isolation and use of hematopoietic and embryonic stem cells. Additionally, the inventors identified the peritoneal cavity as a new source of hematopoietic stem cells. In one embodiment, the invention provides methods of isolating progenitor and/or stem cells from the peritoneal cavity. In another embodiment, the invention provides methods of transporting progenitor and/or stem cells from the peritoneal cavity to another organ. In another embodiment, the present invention provides methods of regenerating bioengineered tissues and/or reconstituting an hematopoietic system.

9 Claims, 31 Drawing Sheets

Figure 22.

|  | Expt#1 | | | | Exp#2 | | | |
| --- | --- | --- | --- | --- | --- | --- | --- | --- |
|  | #4 | | #5 | | #6 | | #7 | |
| M Peri cell | 1.80E+06 | | 1.80E+06 | | 6.00E+05 | | 6.00E+05 | |
| F Sup BM | 5.00E+05 | | 5.00E+05 | | 2.50E+05 | | 2.50E+05 | |
| Harvest | PCT12w | | PCT12w | | PCT12w | | PCT12w | |
| PCR(DNA) | Y-C | β-glo | Y-C | β-glo | Y-C | β-glo | Y-C | β-glo |
| BM | (+) | (+) | (+) | (+) | (++) | (+) | (++) | (+) |
| PB(WBC) | (+) | (+) | (+) | (+) | (++) | (+) | (+) | (+) |
| Heart | (+) | (+) | (+) | (+) | (+) | (+) | (+) | (+) |
| Lung | (+) | (+) | (+) | (+) | (+) | (+) | (+) | (+) |
| Liver | (+) | (+) | (+) | (+) | (+) | (+) | (+) | (+) |
| Spleen | (+) | (+) | (+) | (+) | (+) | (+) | (++) | (+) |
| Kidney | (+) | (+) | (+/-) | (+) | (+) | (+) | (+) | (+) |
| Brain | (-) | (+) | (-) | (+) | (-) | (+) | (-) | (+) |

METHODS FOR ISOLATING AND USING HEMATOPOIETIC AND EMBRYONIC STEM CELLS OF THE PERITONEAL CAVITY

This application is the National Phase of International Application PCT/US08/53725, filed Feb. 12, 2008, which designated the U.S. and that International Application was published under PCT Article 21(2) in English. This application also includes a claim of priority under 35 U.S.C. §119(e) to U.S. provisional patent application No. 60/889,442, filed Feb. 12, 2007.

FIELD OF THE INVENTION

The invention relates generally to the field of stem cells and, more specifically, to peritoneal-derived stem/progenitor cells.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Vascular bypass grafting is the mainstay of revascularization for ischemic heart disease and peripheral vascular disease, and in the US alone 1.4 million arterial bypass operations are performed annually. However, 30% of patients who require arterial bypass procedures do not have saphenous veins suitable for use, because of previous harvest for bypass surgery, varicose degeneration, or inadequate diameter or length (McKee, J. A., Banik, S. S., Boyer, M. J., Hamad, N. M., Lawson, J. H., Niklason, L. E., and Counter, C. M. 2003 *EMBO Rep* 4:633-638). To overcome this limitation, synthetic materials are frequently used for treatment of peripheral vascular disease. However, they are limited to high flow/low resistance conditions (Whittemore, A. D., Kent, K. C., Donaldson, M. C., Couch, N. P., and Mannick, J. A. 1989 *J Vasc Surg* 10:299-305; Faries, P. L., Logerfo, F. W., Arora, S., Hook, S., Pulling, M. C., Akbari, C. M., Campbell, D. R., and Pomposelli, F. B., Jr. 2000 *J Vasc Surg* 32:1080-1090) because of poor elasticity (Gozna, E. R., Mason, W. F., Marble, A. E., Winter, D. A., and Dolan, F. G. 1974 *Can J Surg* 17:176-179 passim), low compliance, and thrombogenicity of synthetic surfaces (Greisler, H. P. 1990 *Ann Vasc Surg* 4:98-103). The artificial materials, when used to bypass arteries of this size, have thrombosis rates greater than 40% after 6 months (Sayers, R. D., Raptis, S., Berce, M., and Miller, J. H. 1998 *Br J Surg* 85:934-938). Despite attempts to improve synthetic polymer grafts, the thrombosis rate has remained high. In addition, foreign body reaction to the synthetic material further confounds the utility of the implants. Recent evidence demonstrates that stem cells can contribute to the regeneration of fibrous tissue in the area of injury. The inventors offer evidence that the mouse peritoneum contains a significant number of stem cells, similar to the level found in bone marrow, which could contribute to formation of fibrous tissue.

A stem cell is a cell type that has a unique capacity to renew itself and give rise to specialized or differentiated cells. Although most cells of the body are committed to conduct a specific function, a stem cell is uncommitted, until it receives a signal to develop into a specialized cell type. What makes the stem cells unique is their proliferative capacity, combined with their ability to become specialized. Somatic stem cells are present in the adult organism. Pluripotency tests have shown that whereas the embryonic or blastocyst-derived stem cells can give rise to all cells in the organism, including the germ cells, somatic stem cells have a more limited repertoire in descendent cell types.

All blood cells that circulate in the peripheral blood are derived from primitive mesenchymal cells referred to as hematopoietic stem cells. In the adult, most of these cells are generally thought to be located in the bone marrow. Hematopoietic stem cells are self regenerating, and also pluripotent in that they differentiate into several lineages, including lymphoid, myeloid and erythroid lineages. It is believed that exposure to growth factors induces a stem cell to be dedicated to differentiate into a specific lineage.

Isolation of progenitor and/or stem cells from the peritoneal cavity has never been described. The identification of the peritoneal cavity as a new source of stem cells with attributes of hematopoietic and embryonic stem cells allows for further discovery of growth factors associated with self-regeneration, as well as growth factors associated with the early steps of dedication of the stem cell to a particular lineage, the prevention of such dedication, and the negative control of stem cell proliferation. The discovery of the peritoneal cavity as a source of stem cells can also be extremely useful as a substitute for bone marrow transplantation, as well as in transplantation of other organs currently performed in association with transplantation of bone marrow. Furthermore, stem cells are important targets for gene therapy, where the inserted genes promote the health of the individual into whom the stem cells are transplanted. Identification of the peritoneal cavity as a new source of stem cells thus provides additional means of isolating cells useful in gene therapy. Isolation of novel hematopoietic stem cell, or a novel intermediate in hematopoiesis, also provides new avenues for treatment of lymphomas and leukemias, as well as other neoplastic conditions. Finally, model systems to isolate and test stem cells and hematopoiesis also provide a means for testing agents that affect stem cells. Thus, there exists a need in the art for identification of new sources of hematopoietic embryonic stem cells.

SUMMARY OF THE INVENTION

Various embodiments provide an isolated progenitor and/or stem cell obtained from a peritoneum of a mammal. The isolated progenitor and/or stem cell, when grafted to an organ, vessel or tissue, may stimulate neovascularization and/or at least partially reconstitute a hematopoietic system of the mammal. The organ, vessel or tissue can be an aorta. The mammal can also be a mouse, or a human.

Further embodiments provide an an isolated hematopoietic progenitor and/or stem cell obtained from a peritoneum of a mammal. The isolated hematopoietic progenitor and/or stem cell, when grafted to an organ, vessel or tissue, stimulates neovascularization and/or at least partially reconstitute a hematopoietic system of the mammal. The mammal can also be a mouse, or a human.

Additional embodiments provide an isolated progenitor and/or stem cell line produced by a process comprising implanting a mechanical substrate in a peritoneum of a mammal, and harvesting a progenitor and/or stem cell from the mechanical substrate. In other embodiments, the harvesting occurs at least 8 weeks after implanting the mechanical substrate. In other embodiments, the mammal can be a mouse, or a human. The process can further comprise of the step of characterizing a stem cell phenotype and/or the step of characterizing a stem cell gene expression profile.

In other embodiments, the invention provides a composition comprising an isolated stem cell obtained from a peritoneum of a mammal. The mammal can also be a mouse or a human. When grafted to an organ, vessel or tissue, the stem cell may regenerate bioengineered tissue and/or at least partially reconstitute a hematopoietic system of the mammal. In another embodiment, a genome of the stem cell has been altered by the insertion and/or deletion of a region of a nucleic acid.

Various embodiments provide a stem cell line based on an isolated stem cell obtained from a peritoneum of a mammal. When grafted to an organ, vessel or tissue, the progenitor and/or stem cell line at least partially reconstitutes a hematopoietic system of a mammal, such as a mouse or human. In other embodiments, the progenitor and/or stem cell line has a genome that has been altered by insertion and/or deletion of a region of a nucleic acid.

Other embodiments include a method of generating a capsule graft comprising implanting a mechanical substrate in a peritoneum of a mammal and harvesting the capsule graft from the mechanical substrate. In some embodiments, the harvesting could occur at least 8 weeks after implanting the mechanical substrate in the peritoneum.

Additional embodiments provide a method of treating heart disease comprising administering a therapeutically effective amount of stem cells where the stem cells are isolated from a peritoneum of a mammal. In other embodiments, the mammal could be a mouse or a human.

Other features and advantages of the invention will become apparent from the following detailed description, taken in conjunction with the accompanying drawings, which illustrate, by way of example, various embodiments of the invention.

BRIEF DESCRIPTION OF FIGURES

Exemplary embodiments are illustrated in referenced figures. It is intended that the embodiments and figures disclosed herein are to be considered illustrative rather than restrictive.

FIG. 20, lanes 9-11 and 12-14 shows β-globin control for the peritoneal-derived cells and bone marrow derived cells, respectively. The data shows that the bone marrow of the transplanted animals contains a population from the donor cells of peritoneal-derived origin.

FIG. 22 depicts a table of competitive repopulating activity of peritoneal progenitor cells in accordance with various embodiments of the present invention.

DESCRIPTION OF INVENTION

Figure 1:
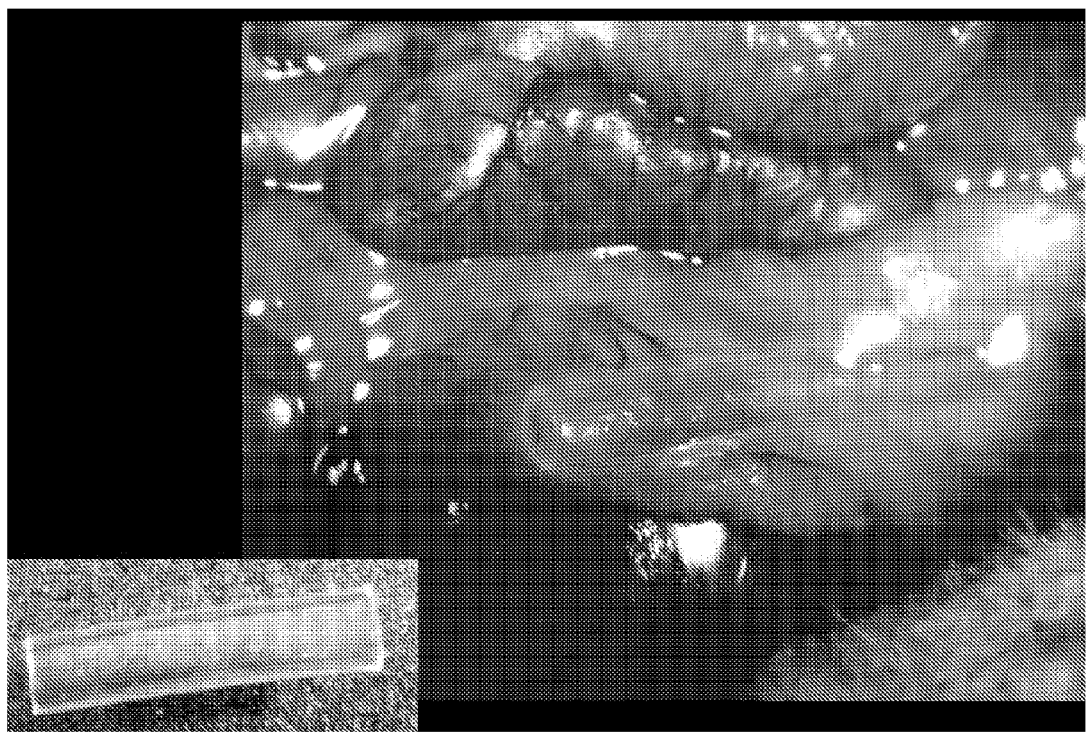
FIG. 1 depicts a polyethylene tubing that has been implanted into a mouse peritoneal cavity after one month in accordance with various embodiments of the present invention. A picture of the tubing by itself is in the bottom left of the figure.
Figure 2:
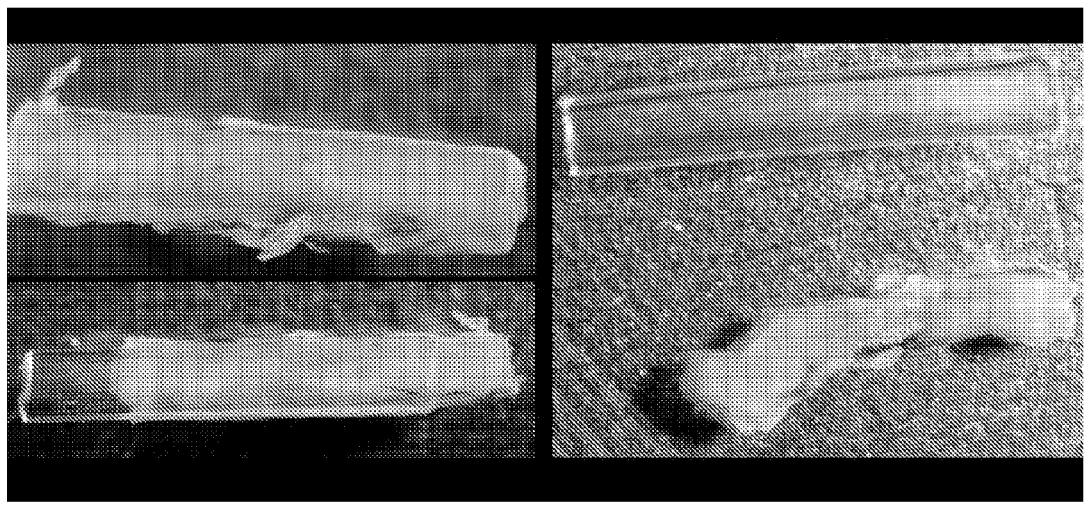
FIG. 2 depicts vascular tissue engineering in accordance with various embodiments of the present invention. The polyethylene tubing has been inserted in the peritoneal cavity for a period of time, then removed.
Figure 3:
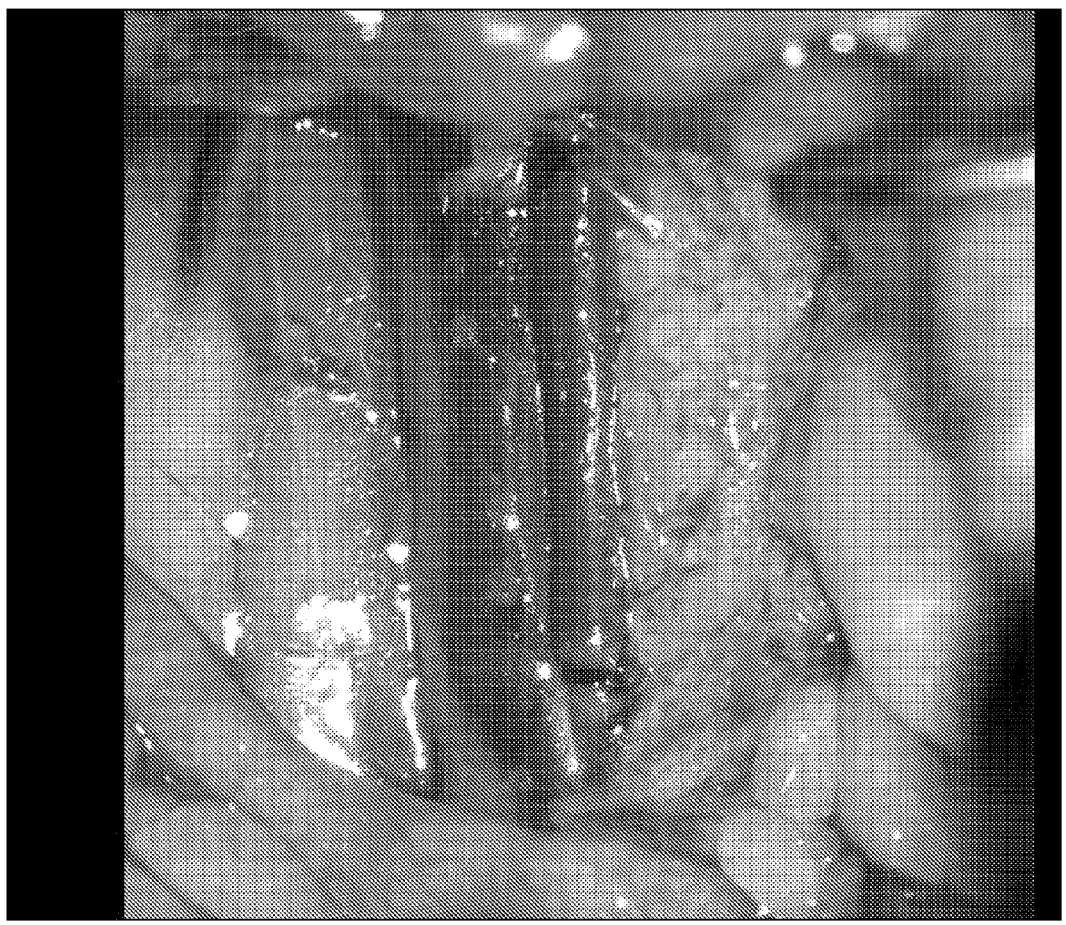
FIG. 3 depicts the grafting of artificially-engineered tissue into the abdominal aorta in accordance with various embodiments of the present invention.
Figure 4:
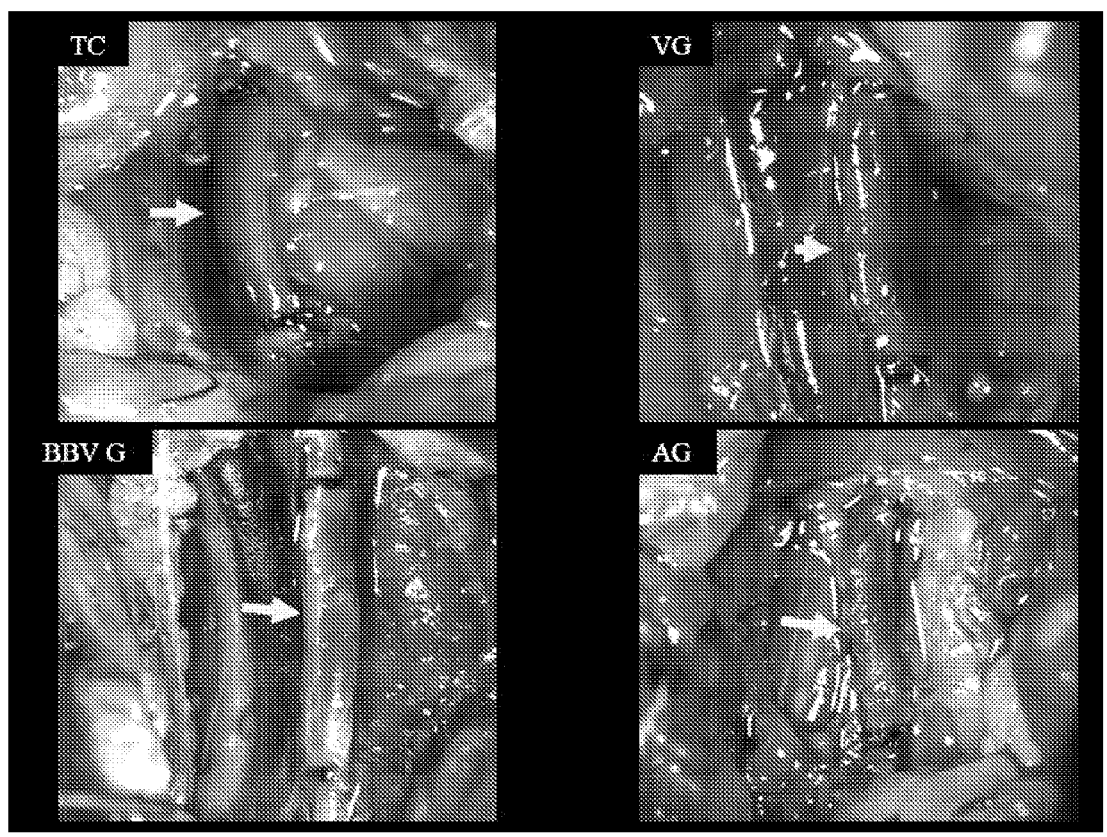
FIG. 4 depicts grafts in the abdominal aorta in accordance with various embodiments of the present invention. "VG" depicts a vein graft; "AG" depicts an artery graft; "TC" depicts a tissue capsule graft; "BBV G" depicts a BBV graft.
Figure 5:
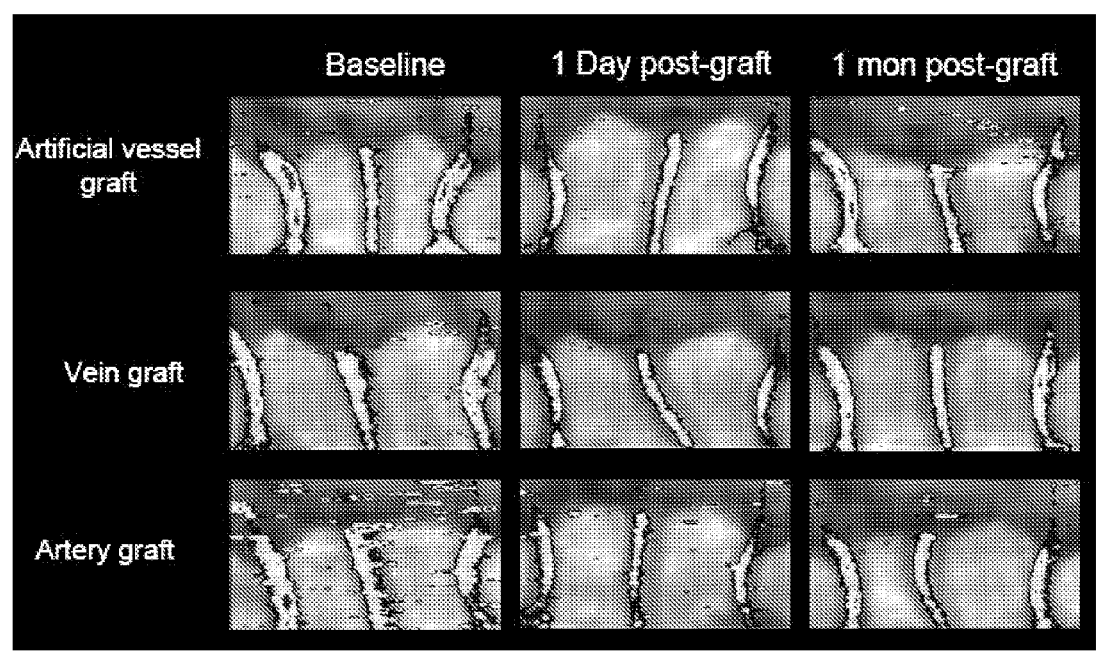
FIG. 5 depicts laser doppler images of bilateral hindlimbs blood flow, including images after grafting, in accordance with various embodiments of the present invention.
Figure 6:
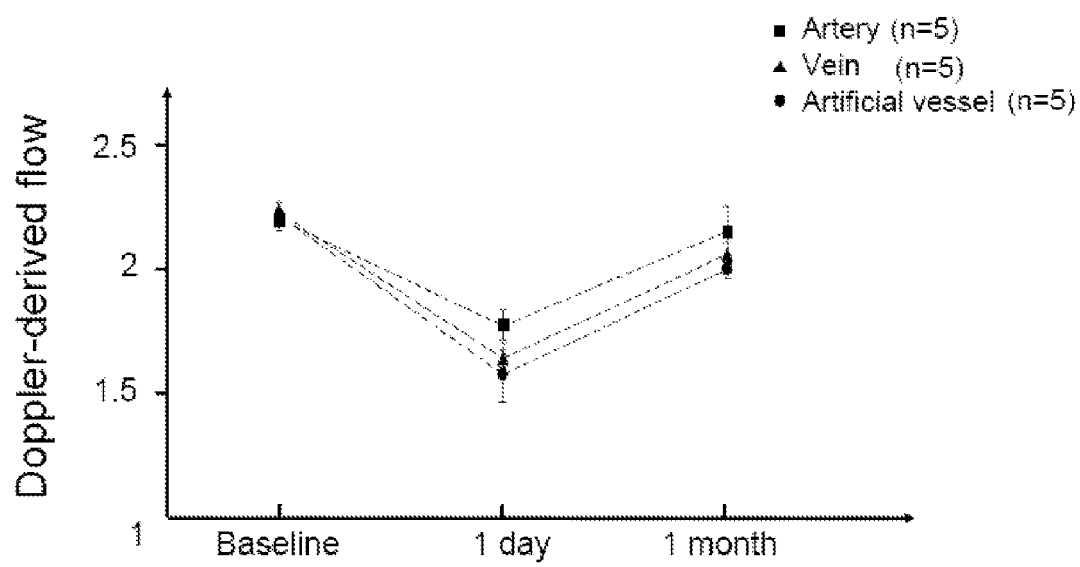
FIG. 6 depicts a chart of the quantification of bilateral hindlimbs blood flow after surgery in accordance with various embodiments of the present invention.
Figure 7:
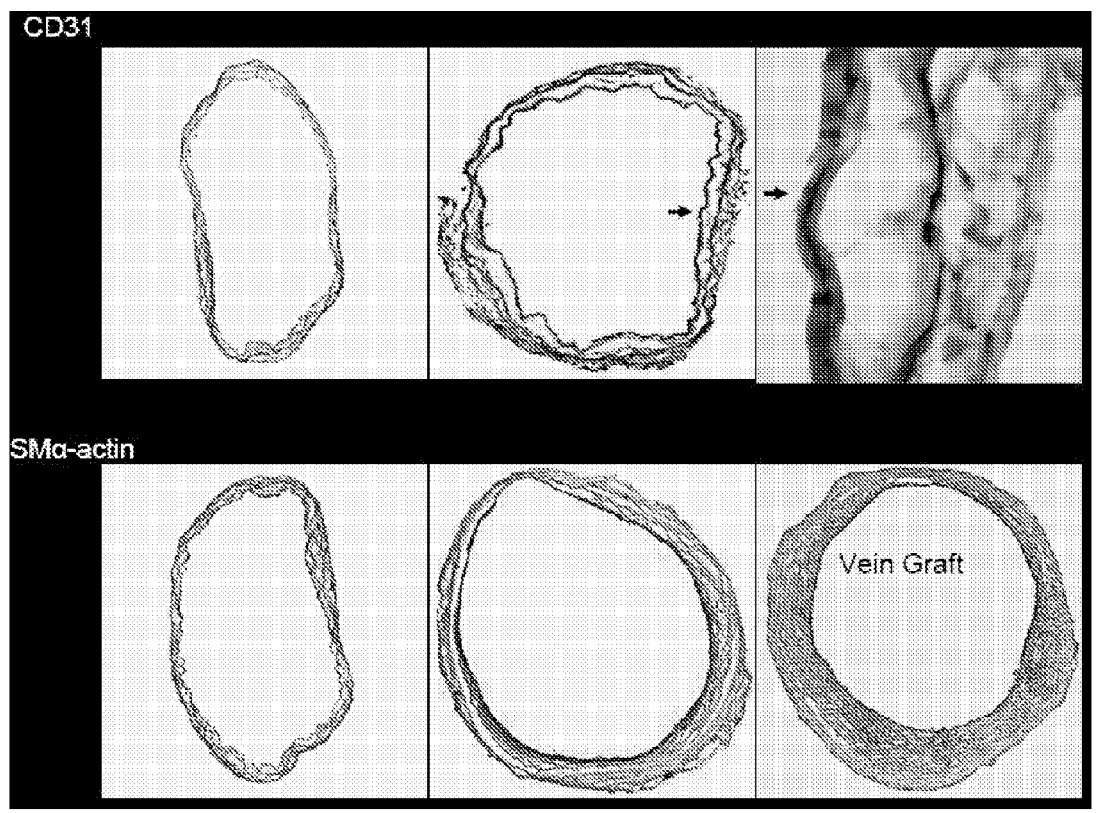
FIG. 7 depicts immunohistochemical stains of tissue after grafting in accordance with various embodiments of the present invention. The top portion is stained using CD31 antibodies and the bottom is stained using SMα-actin antibodies, an early smooth muscle marker.
Figure 8:
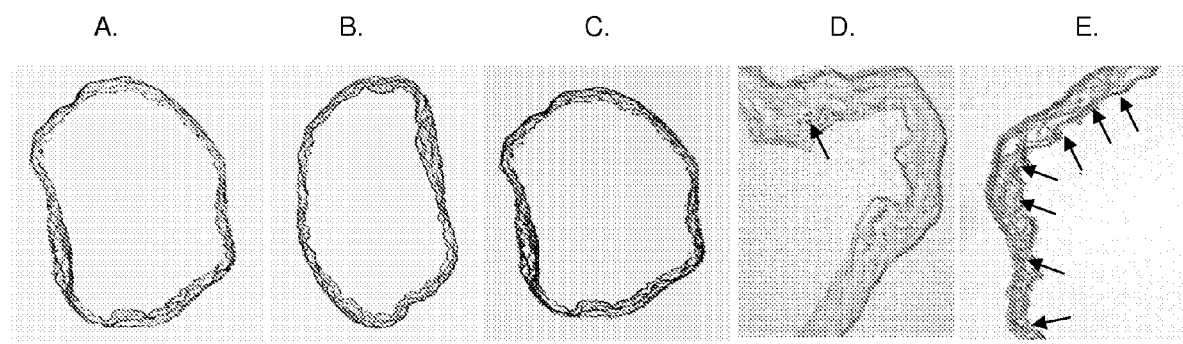
FIG. 8 A-E depicts immunostaining analysis of capsules harvested at 8 weeks post-implantation in the peritoneal cavity of C57BL/6 and BALB/c strains in accordance with various embodiments of the present invention. The figure depicts one or two layers of cells that are not distributed evenly throughout the capsules. Neither smooth muscle α-actin (FIG. 8A) nor anti-CD31 (FIG. 8B) antibodies stained the sections. However, collagen staining revealed that the capsules are composed of collagenous material (FIG. 8C). Anti-MOMA-2 antibody staining revealed that the tissue capsules had few, if any, macrophages; they were observed in only one of the capsules prior to grafting (FIG. 8D, arrow). Since the inventors found stem/progenitor cells in the mouse peritoneum, as described herein, the inventors concluded that these cells, in part, contribute to the formation of tissue capsules. To explore this, the inventors stained harvested capsules with anti-stem cell antigen-1 (Sca-1) antibody. Immunostaining showed that the tissue capsule cells express Sca-1 antigen suggesting that they have phenotype of primitive cells (FIG. 8E, arrows). As further described herein, microarray analysis of total RNA isolated from freshly-isolated capsules proves this notion.
Figure 9:
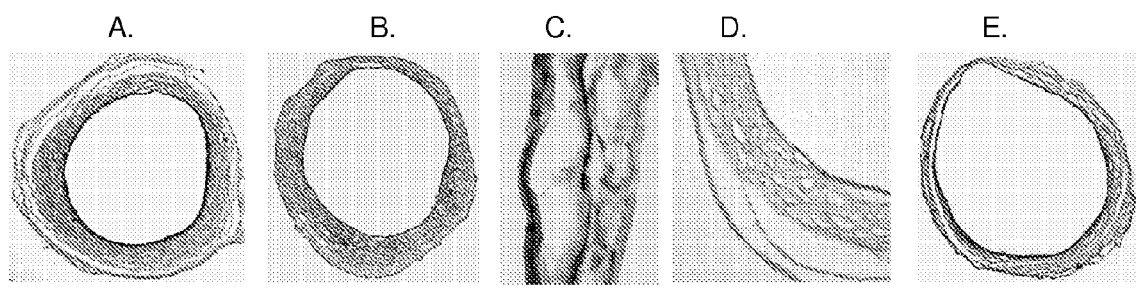
FIG. 9 A-E depicts immunohistological analysis of capsule auto-grafts harvested 4 weeks after grafting into abdominal aorta of C57BL/6, BALB/c and MRL mice in accordance with various embodiments of the present invention. The stains reveal that the thickness of the capsule grafts increased compared to the freshly harvested capsule; IE the grafts have been arterialized. While cells in the harvested tissue capsule did not express markers of smooth muscle cell or endothelial cells (see FIGS. 8A and 8B, disclosed herein), the capsule graft cells expressed these falls as evident in FIG. 9. Anti smooth muscle α-actin antibody strongly stained the cells in the vessel wall of capsule grafts (FIG. 9A), similar to the positive control vein graft (FIG. 9B). Anti-CD31 staining showed that endothelial cells lined the lumen of the capsule grafts (FIG. 9C). Anti-MOMA-2 antibody stained few macrophages, if any, in the capsule grafts (FIG. 9D). To determine whether stem/progenitor cells that were detected in the freshly harvested tissue capsule (see FIG. 8E, disclosed herein) are present in the capsule grafts, sections were stained with anti-Sca-1 antibody. Immunostaining showed that some cells in the lumen and capsule wall of the grafts contain stem cell (FIG. 9E). Collectively, these results show that the tissue capsule undergoes arterialization when exposed to arterial pressure, possibly in response to pulsatile flow, and the primitive cells contribute to this remodeling.
Figure 10:
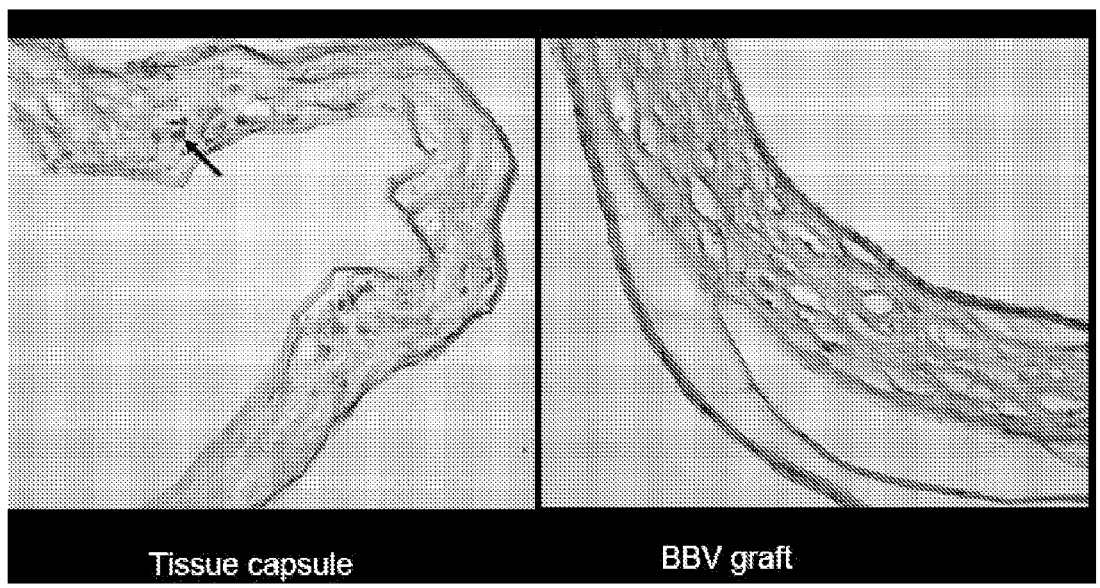
FIG. 10 depicts MOMA-2 immunohistochemical stains made after grafting in accordance with various embodiments of the present invention. The left figure depicts tissue capsule, the right figure depicts BBV graft.
Figure 11:
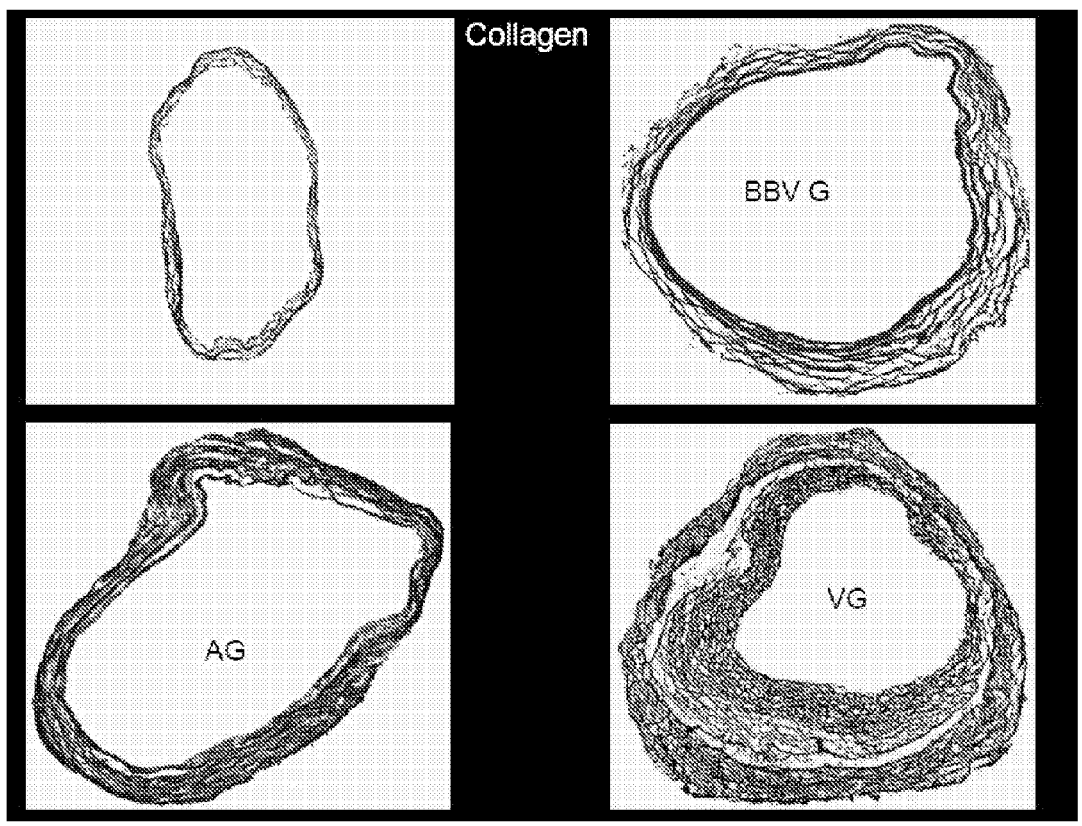
FIG. 11 depicts collagen immunohistochemical stains made after grafting in accordance with various embodiments of the present invention.
Figure 12:
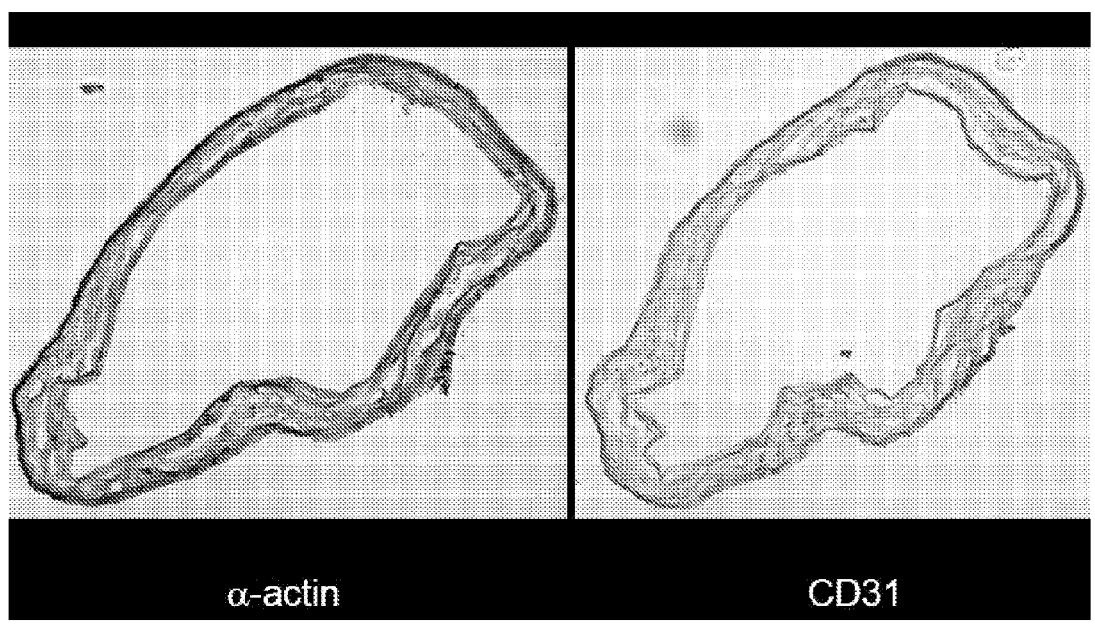
FIG. 12 depicts immunostaining of peritoneal tissue before grafting in accordance with various embodiments of the present invention. The left figure depicts immunostaining with antibodies specific for α-actin. The right figure depicts immunostaining with antibodies specific for CD31.
Figure 13:
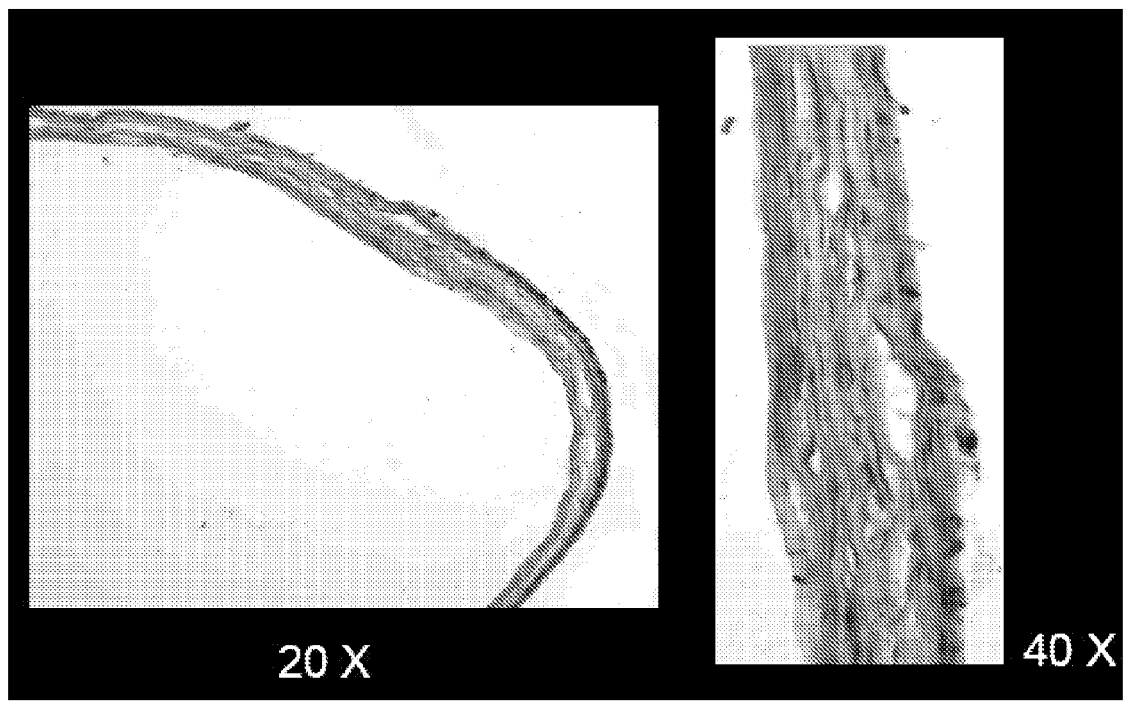
FIG. 13 depicts immunostaining after grafting in accordance with various embodiments of the present invention. The left picture depicts 20× magnification, and the right picture depicts 40× magnification. The figure shows smooth muscle α-actin expression after grafting.
Figure 14:
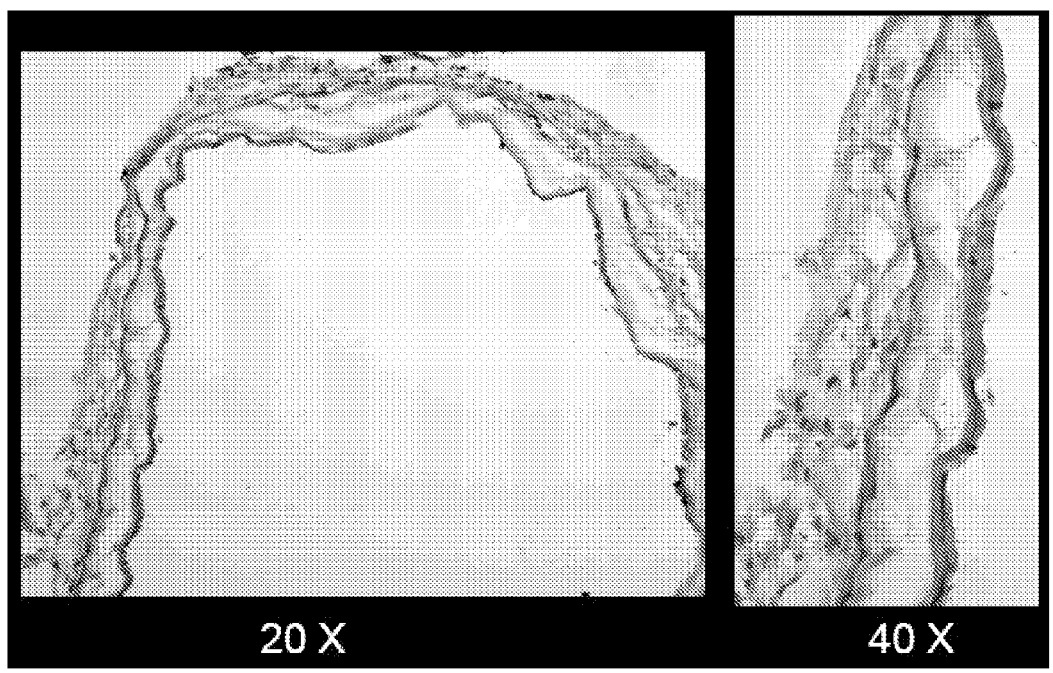
FIG. 14 depicts immunostaining after grafting in accordance with various embodiments of the present invention. The left picture depicts 20× magnification, and the right picture depicts 40× magnification. The figure shows CD31 expression after grafting.
Figure 15:
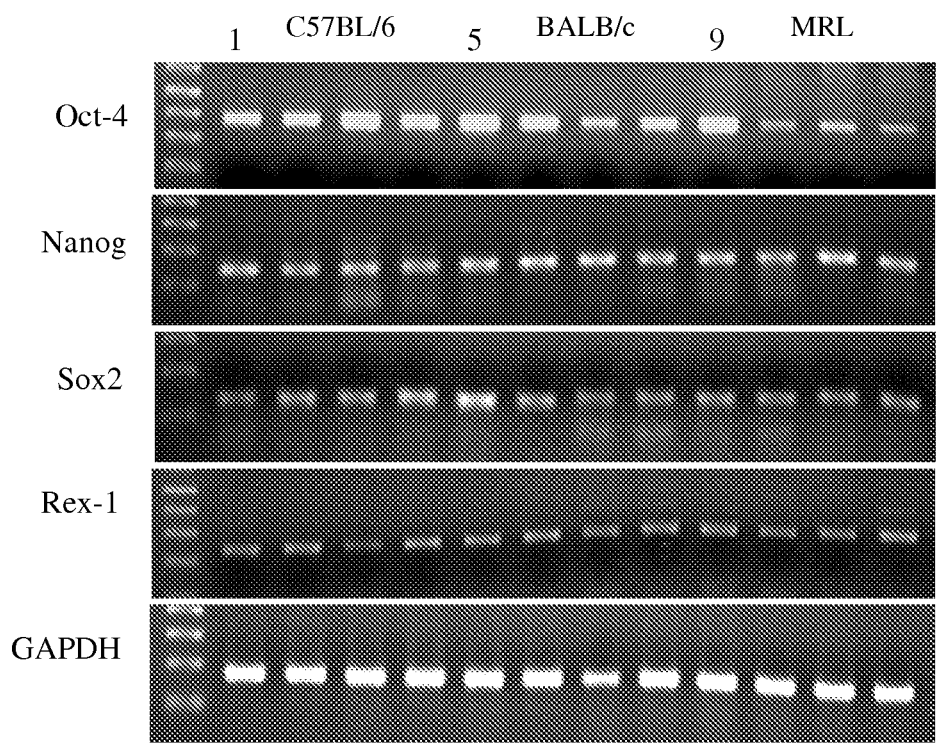
FIG. 15 depicts expression of stem-cell specific transcription factors in peritoneal cells in accordance with various embodiments of the present invention. Total RNA was isolated from peritoneal cells of 4 C57BL/6 (FIG. 15, lanes 14), 4 BALB/c (FIG. 15, lanes 5-8), and 4 MRL mice (FIG. 15, lanes 9-12). 4 mice were used for each strain. The RNA was subjected to RT-PCR analysis using specific primers for the transcription factors. Glyceraldehyde-3-phosphate dehydrogenase (GAPDH) was used as an internal standard. The amplified products were separated on 1.2% agarose gels and stained with ethidium bromide.
Figure 16:
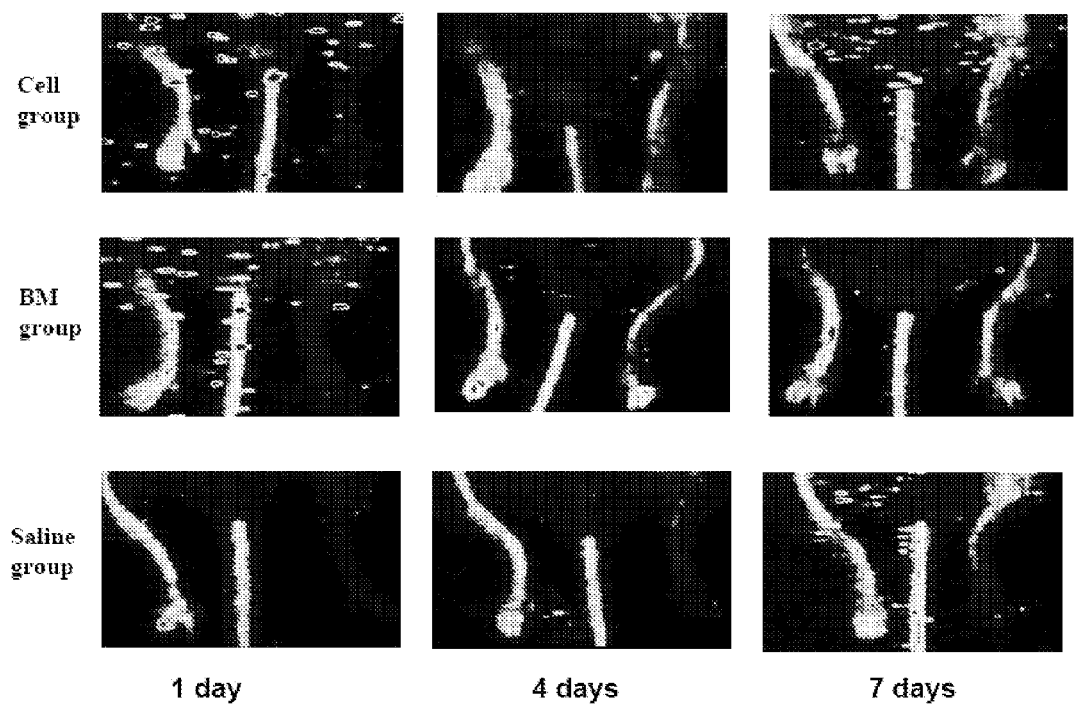
FIG. 16 depicts the bio-effect of peritoneal cell with laser doppler perfusion images in MRL mice in accordance with various embodiments of the present invention. The figure demonstrates an ability to promote reperfusion of ischemic hindlimb.
Figure 17:
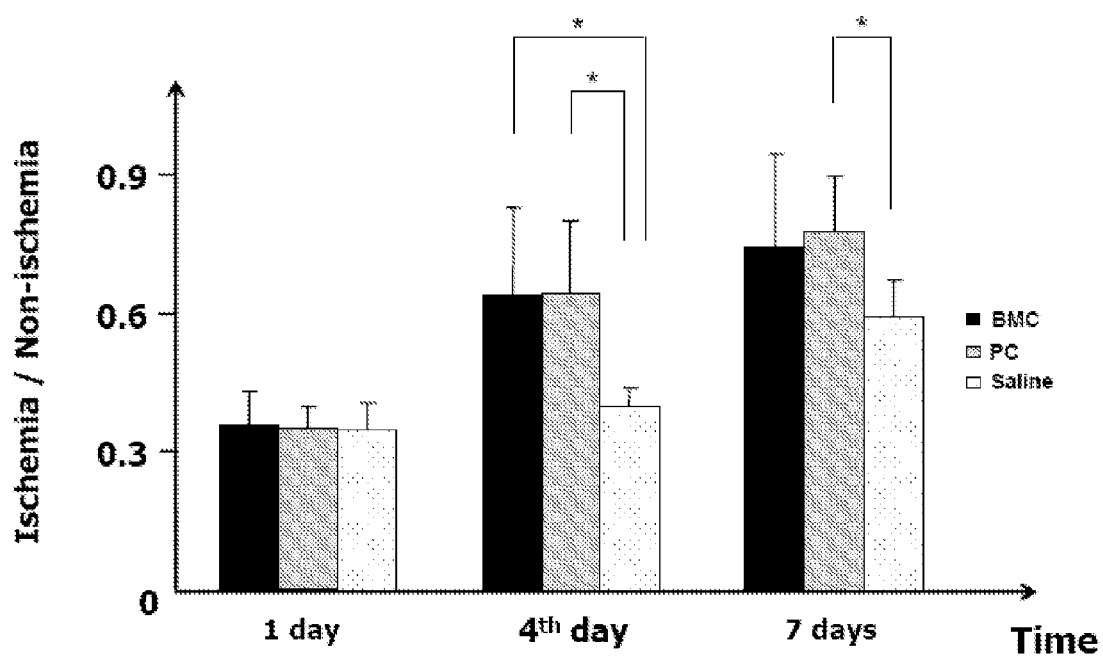
FIG. 17 depicts a graph of the bio-effect of peritoneal cell with laser doppler perfusion images in MRL mice in accordance with various embodiments of the present invention. The figure demonstrates an ability to promote reperfusion of ischemic hindlimb.
Figure 18:
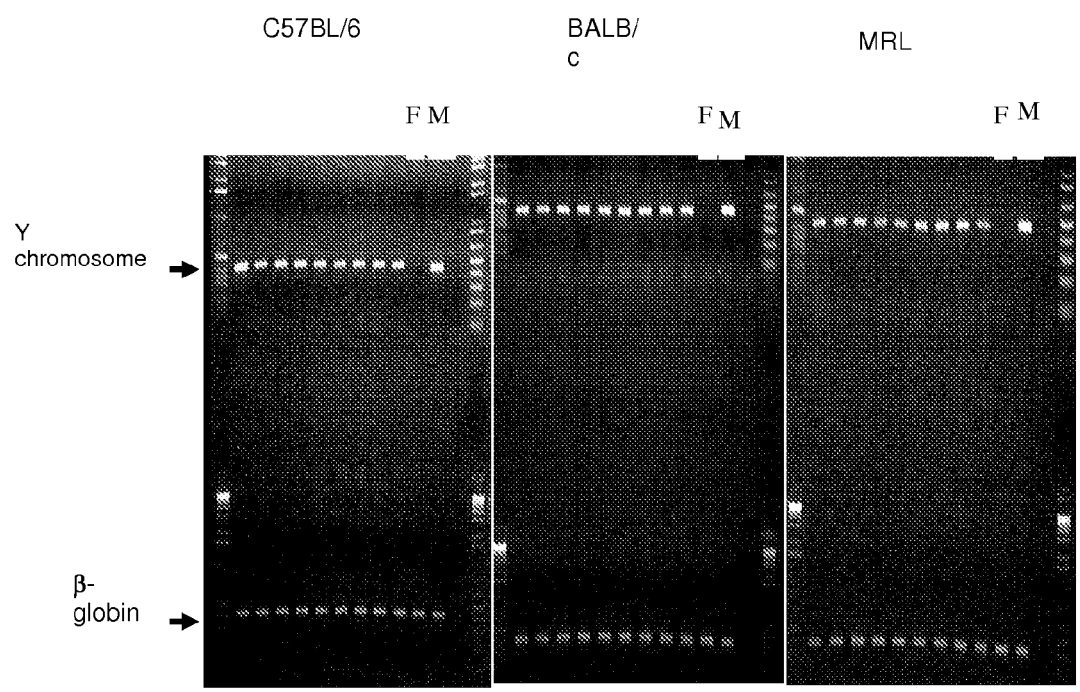
FIG. 18 depicts peritoneal cells reconstitute hematopoietic system of lethally irradiated mice in accordance with various embodiments of the present invention. The inventors performed competitive repopulation using the sex-mismatch system. The results show the detection of the Y chromosome in all recipient mice. DNA was isolated from white blood cells of each recipient mouse (10 mice/group), and analyzed with PCR using Y chromosome primers. The β-globin was used to control for loading. White blood cells isolated from female (F) and male (M) mice were used as negative and positive controls.
Figure 19:
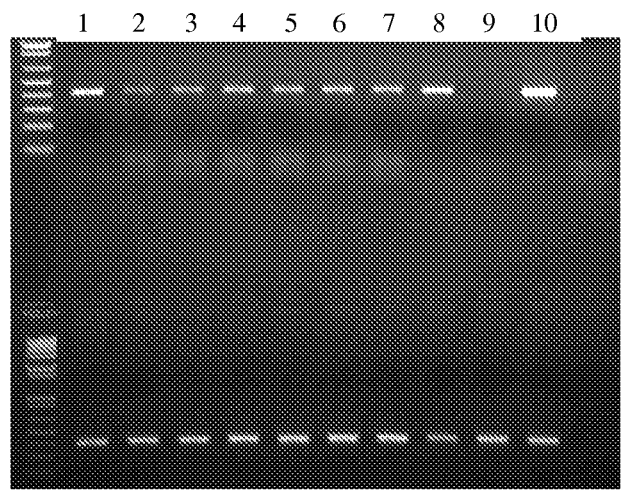
FIG. 19 depicts peritoneal cells engraft to various organs in accordance with various embodiments of the present invention. The inventors detect Y chromosome in the organ of primary recipient mice. PCR analysis of genomic DNA isolated from various organs of recipient mice found Y-chromosome in bone marrow (FIG. 19, lane 1), brain (FIG. 19, lane 2), heart (FIG. 19, lane 3), kidney (FIG. 19, lane 4), liver (FIG. 19, lane 5), lung (FIG. 19, lane 6) spleen (FIG. 19, lane 7), and white blood cells (FIG. 19, lane 8). The chromosome isolated from negative control female mice and positive control male mice are shown in FIG. 19, lanes 9 and 10, respectively. The β-globin has been used as a loading control (FIG. 19, lower lanes). These data show that that engraftment occurred in the various organs of all 10 recipient mice transplanted with the peritoneal cells.
Figure 20:
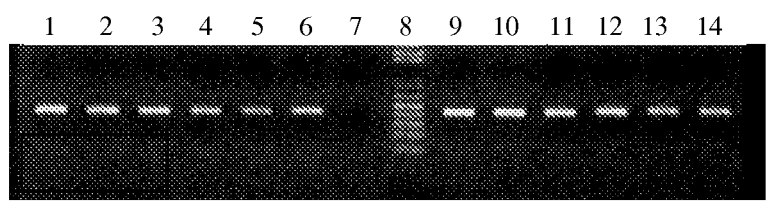
FIG. 20 depicts peritoneal-derived cells proliferate and differentiate in the secondary recipient host in accordance with various embodiments of the present invention. As true stem cells must be highly proliferative and able to generate progeny that can repopulate secondary recipients, the bone marrow harvested 4 months after the primary transplantation was used for secondary transplantation. After 4 months of secondary transplantation, the peripheral blood was collected by retro-orbital bleeding from 3 recipient mice that were originally transplanted with male peritoneal-derived cells (primary transplant) and 3 recipient mice that were originally transplanted with male bone marrow cells (primary transplant, positive control). The PCR analysis of the collected blood from 3 peritoneal-derived recipient mice (FIG. 20, lanes 1-3) and 3 bone marrow recipient mice (FIG. 20, lanes 4-6) shows the presence of Y-chromosome in all mice groups. The female bone marrow was used as a negative control (FIG. 20, lane 7).
Figure 21:
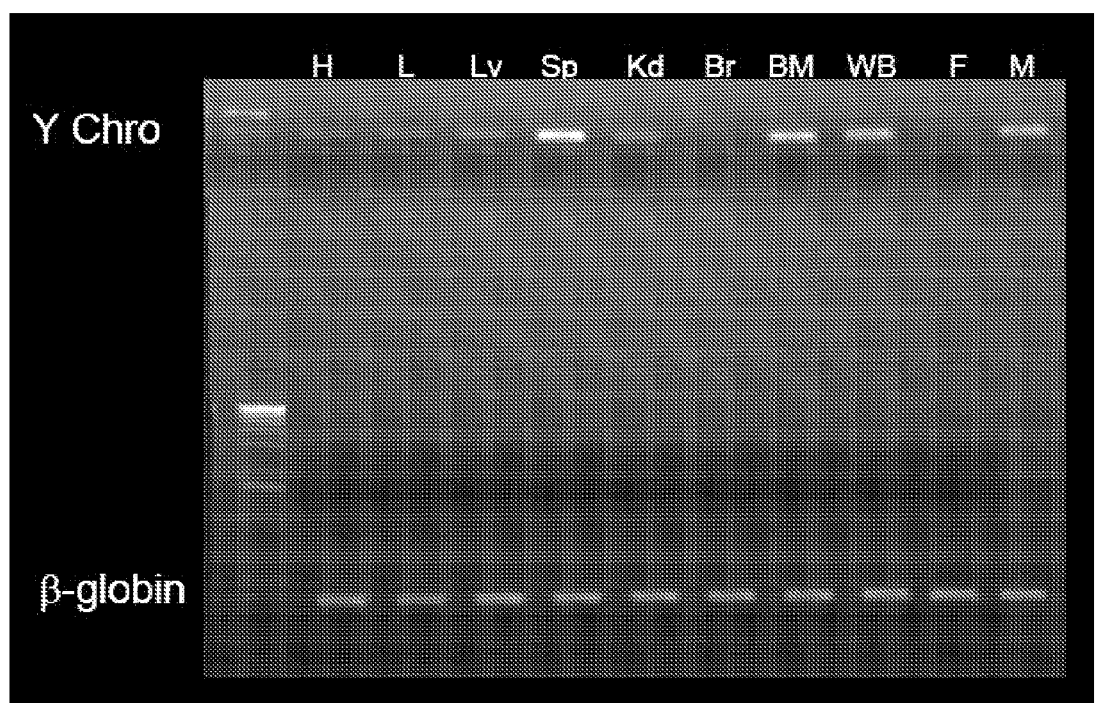
FIG. 21 depicts competitive repopulating activity of peritoneal progenitor cells in accordance with various embodiments of the present invention. "H" denotes heart, "L" denotes lung, "Lv" denotes liver, "sp" denotes spleen, "Kd" denotes kidney, "Br" denotes brain, "F" denotes female, "M" denotes male.
Figure 23:
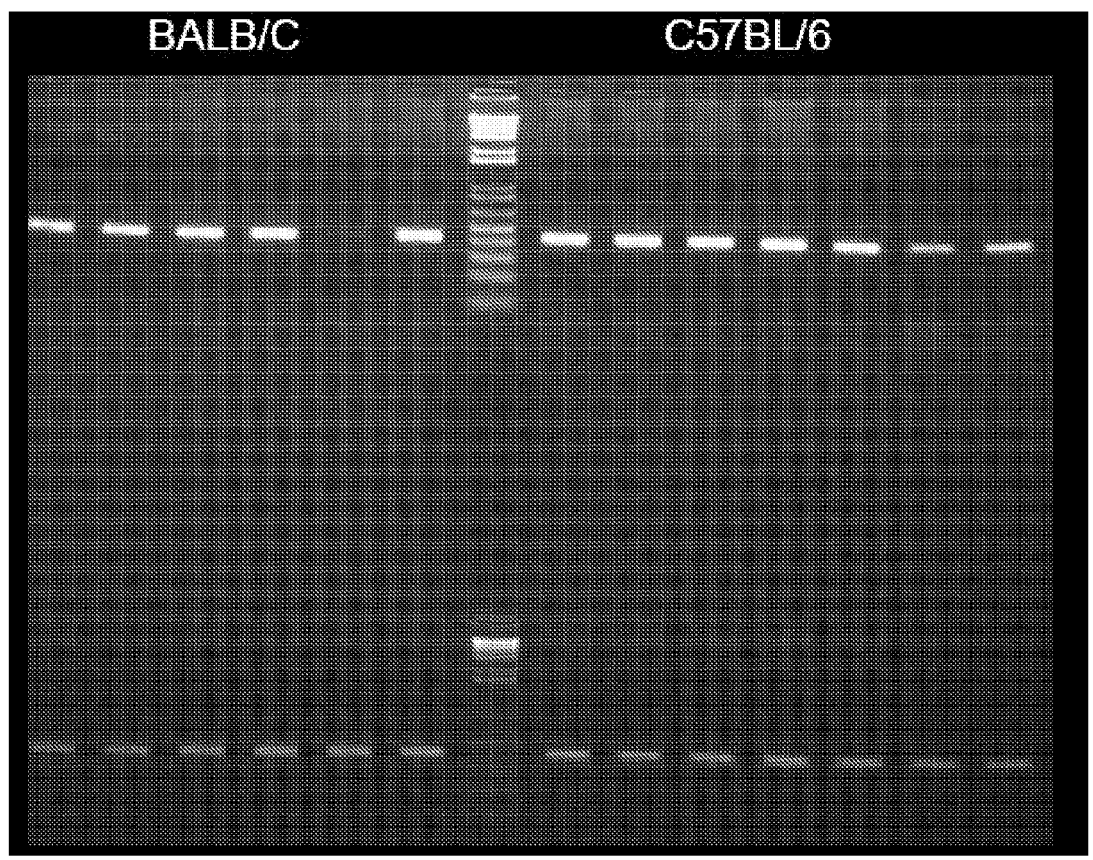
FIG. 23 depicts sex mismatch bone marrow transplantation (positive control) in accordance with various embodiments of the present invention. "BALB/C" depicts fragments from the BALB/C strain of mice; "C5BL/6" depicts fragments from the C5BL/6 strain of mice.
Figure 24:
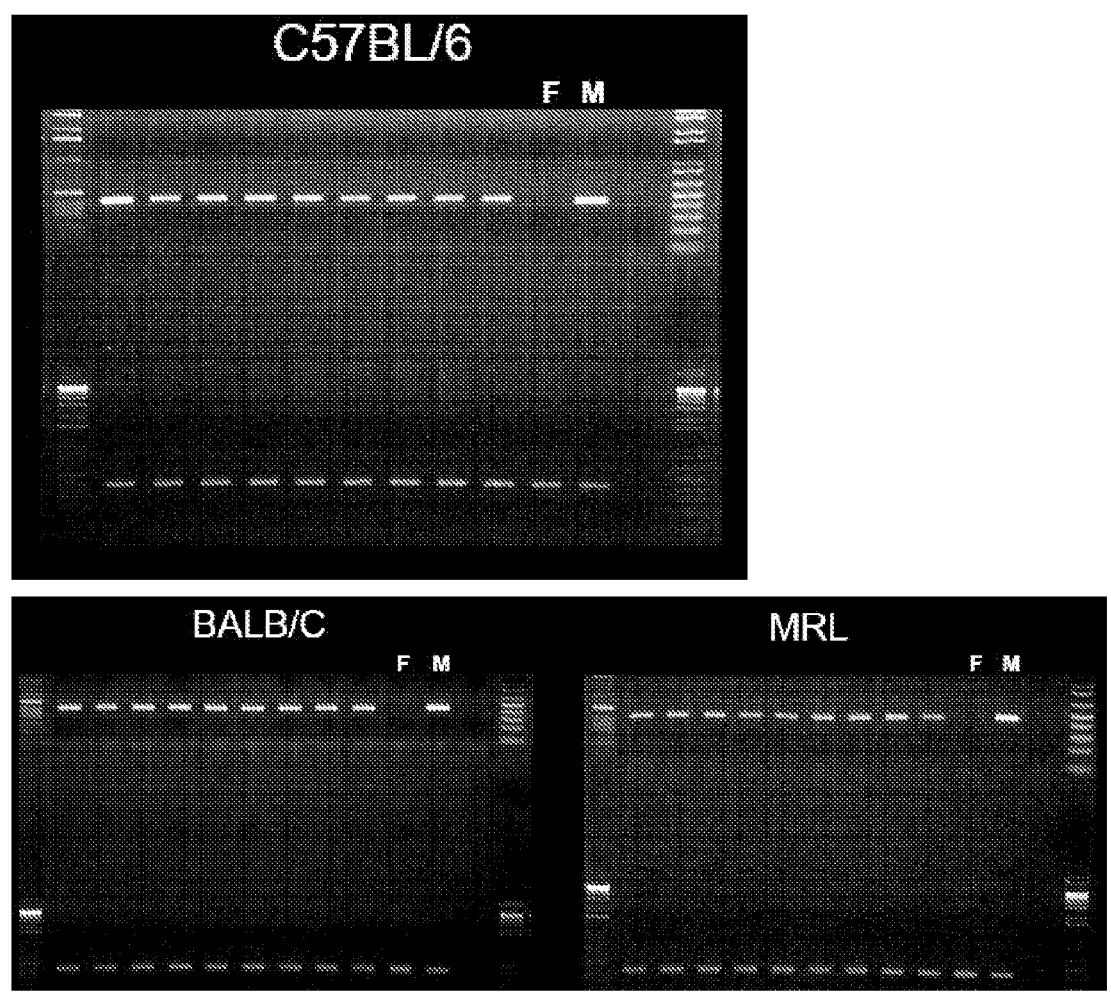
FIG. 24 depicts engraftment of peritoneal progenitor cells in different strains of mice in accordance with various embodiments of the present invention.
Figure 25:
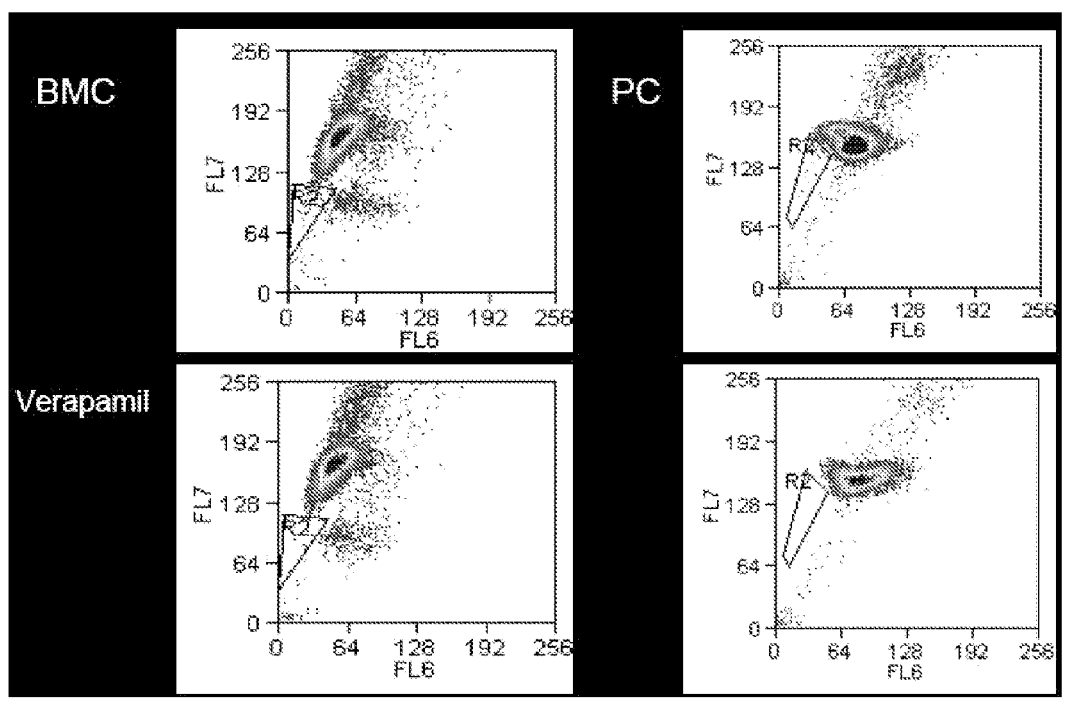
FIG. 25 depicts representative FACS profile of C56BL/6 peritoneal and bone marrow cells after staining with Hoechst dye in accordance with various embodiments of the present invention. To establish whether peritoneal cells isolated from C57BL/6 mice have characteristics of side population cells, peritoneal cells were treated with Hoechst 33342 and then analyzed by FACS. Bone marrow cells were used as a positive control. To determine the specificity of dye uptake, cells were treated with Hoechst in the presence of verapamil, an inhibitor of ABCG2 transporter, which prevents effluxing the dye. The treatment with verapamil abalated side population cells in both peritoneal cells (PC) and bone marrow cells (BMC). The data shows that the peritoneal cells are heterogenous and contain a subpopulation of cells, which possess the characteristics of stem/progenitor cells.
Figure 26:
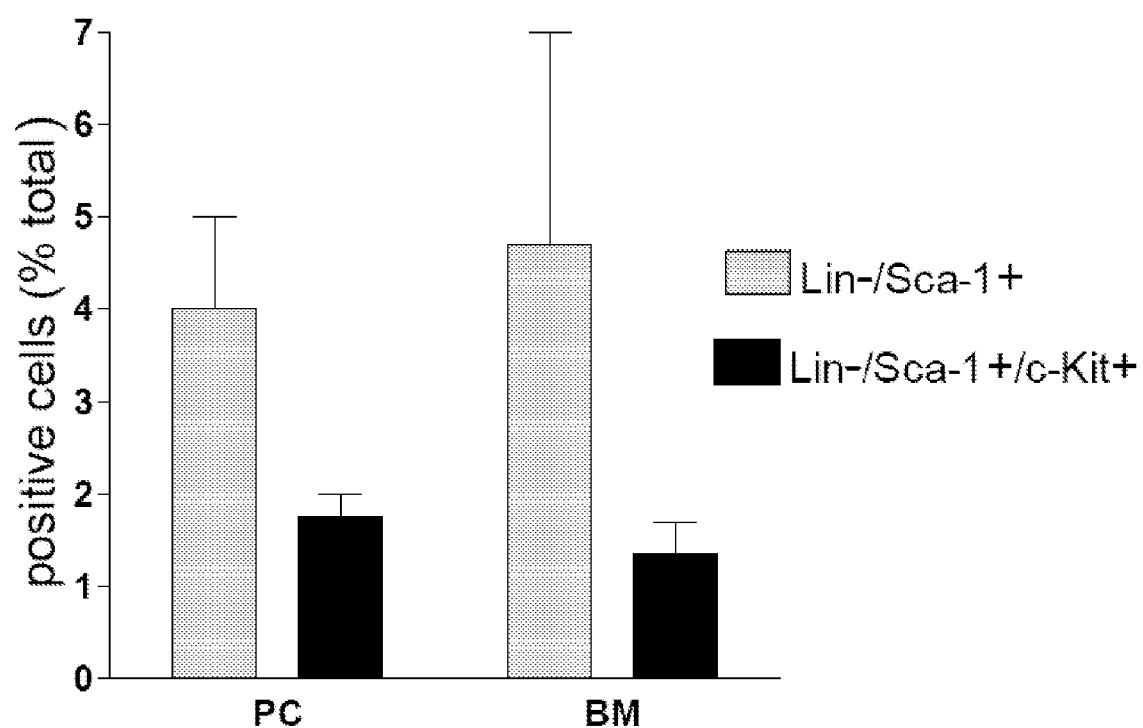
FIG. 26 depicts a chart of phenotype of peritoneal cells in accordance with various embodiments of the present invention. When compared to total cells, the percentage of lineage negative/Sca-1 positive cells in the peritoneal cells (PC) and bone marrow cells (BM) are 4±1% and 4.7±2.3%, respectively. When the expression of both Sca-1 and c-kit antigens were measured, the number of positive cells was decreased, 1.6±0.1% for PC cells and 1.9±0.2% for BM cells. The number of Lin$^-$/Sca-1$^+$/c-kit$^+$ in peritoneal cells is comparable to those in the positive control bone marrow cells. These results confirm previous side population studies described herein and show that the peritoneal cells are heterogeneous and there is a subpopulation of cells with a stem cell phenotype. The inventors can isolate approximately $1 \times 10^3$-$5 \times 10^3$ Lin$^-$/Sca-1$^+$/c-kit$^+$ from freshly isolated peritoneal cells from each stain of mice. Generally, the MRL stain produced 20±10% more LSK cells than C57BL/6 or BALB/c mouse strains.
Figure 27:
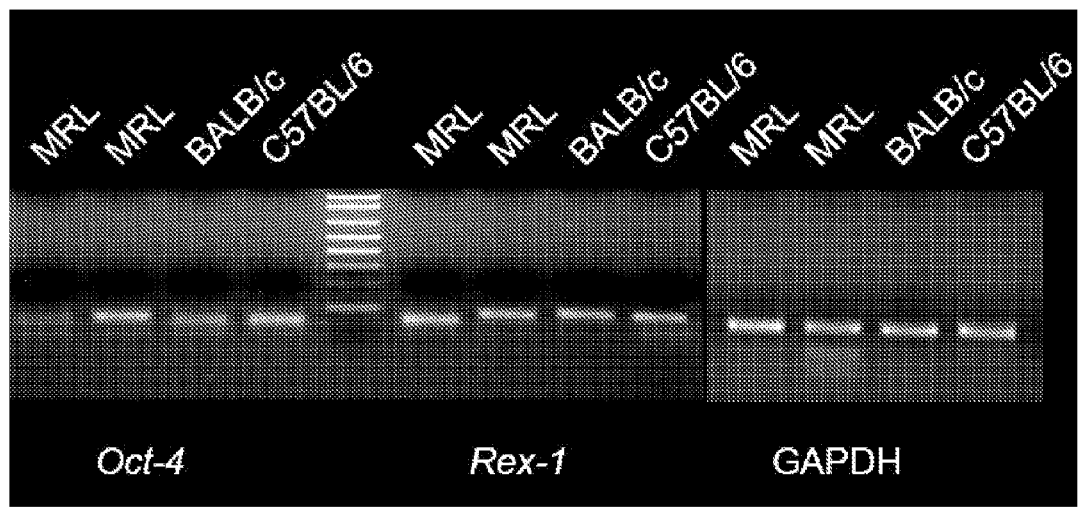
FIG. 27 depicts embryonic stem cell markers (Oct-4, Rex-1, GAPDH) in PC in accordance with various embodiments of the present invention.
Figure 28:
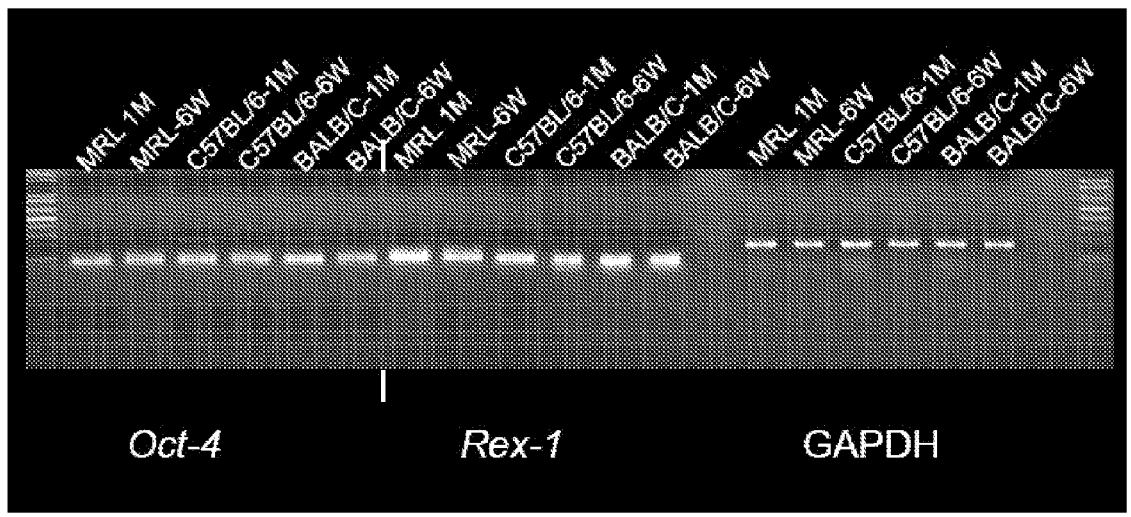
FIG. 28 depicts embryonic stem cell markers (Oct-4, Rex-1, GAPDH) in cultured PC in accordance with various embodiments of the present invention.
Figure 29:
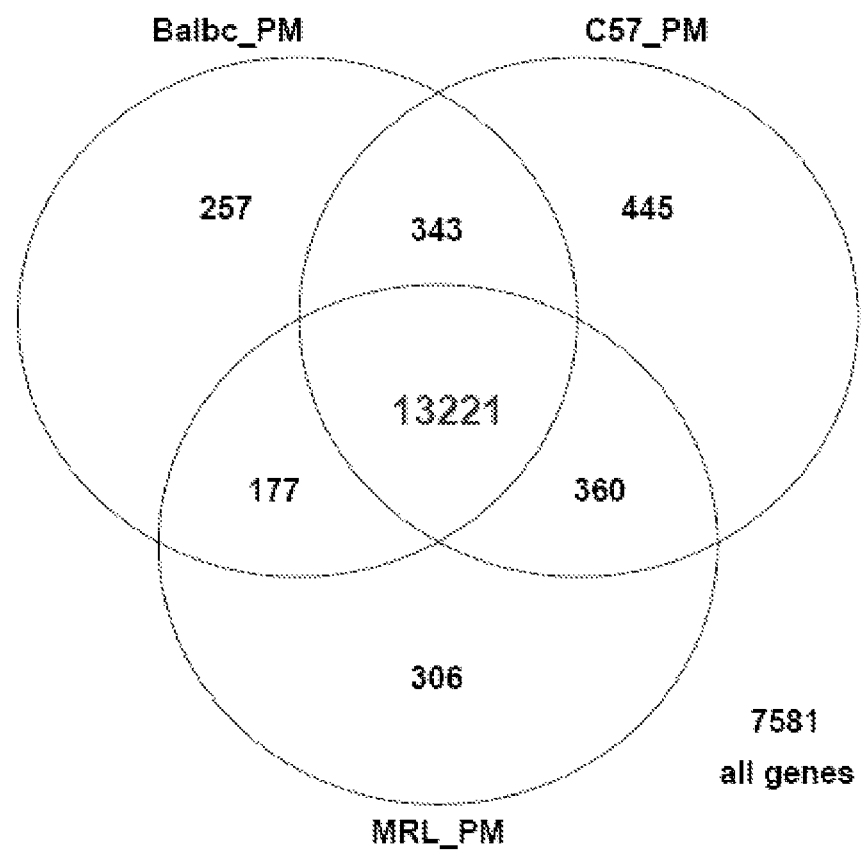
FIG. 29 depicts a venn diagram of probe sets present in 3 strains in accordance with various embodiments of the present invention.
Figure 30:
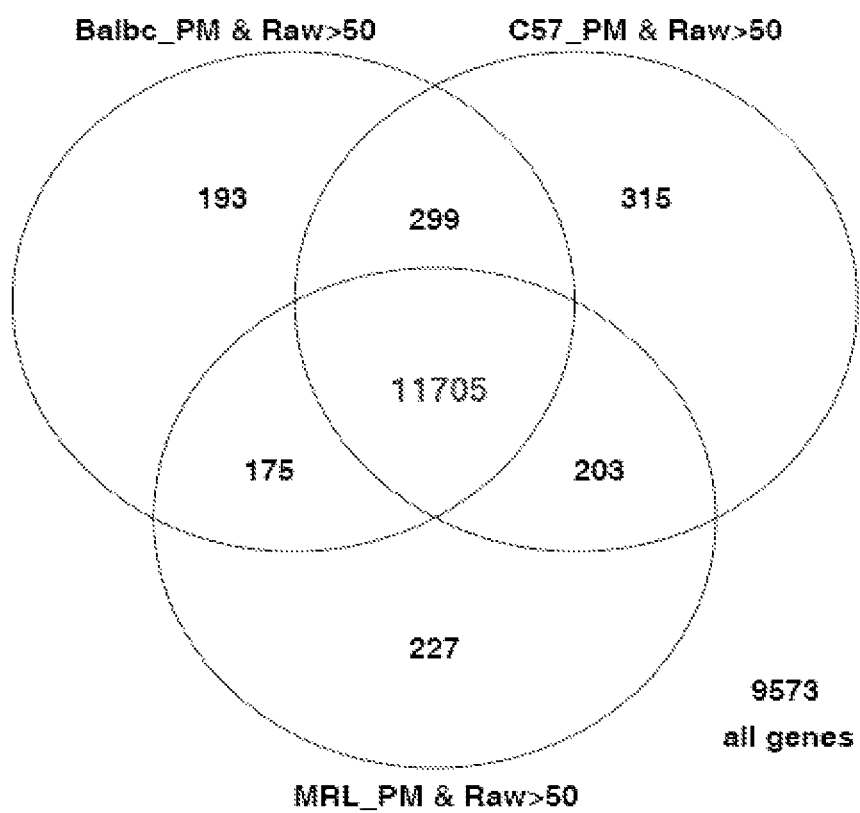
FIG. 30 depicts a venn diagram of probe sets present and raw signal >50 in 3 strains in accordance with various embodiments of the present invention.
Figure 31:
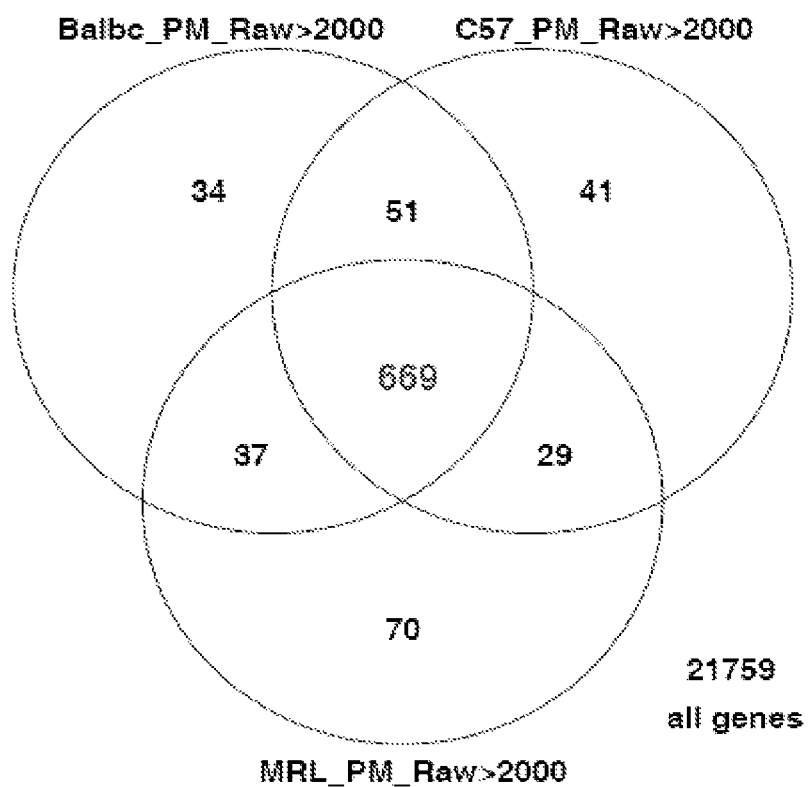
FIG. 31 depicts a venn diagram of probe sets present and raw signal >2,000 in 3 strains in accordance with various embodiments of the present invention. The venn diagram shows the number of genes enriched in each strain-specific cell population and their overlaps. There is a high overlap between the 3 strains of mice. In a small percentage of the cases, the same gene is recognized by more than one probe set in the Affymetrix array. Thus, the 669 probe sets enriched in all peritoneal cells actually corresponds to 628 unique genes.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994); March, *Advanced Organic Chemistry Reactions, Mechanisms and Structure* 4th ed., J. Wiley & Sons (New York, N.Y. 1992); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Autograft" as used herein refers to tissue grafts transplanted from one body site to another in the same organism.

"Stem cell" as used herein refers to a cell that can continuously produce unaltered daughters and also has the ability to produce daughter cells that have different, more restricted properties. Stem cells include adult and embryonic stem cells.

"Progenitor cell" as used herein refers to a parent cell that gives rise to a distinct cell lineage by a series of cell divisions.

"Progenitor and/or stem cell" as used herein refers to a cell that may have partial or full attributes of progenitor cells, or stem cells, or attributes commonly shared by both stem cells and progenitor cells.

"Mammal" as used herein refers to any warm-blooded vertebrate animal of the class Mammalia.

"Mechanical substrate" as used herein may be understood to include any suitable material, template, substrate, or component, which may for example include plastic tubing.

"Packaging material" as used herein refers to one or more physical structures used to house the contents of a kit, such as inventive compositions and the like. The packaging material is constructed by well known methods, preferably to provide a sterile, contaminant-free environment.

"Package" as used herein refers to a suitable solid matrix or material such as glass, plastic, paper, foil, and the like, capable of holding individual kit components. Thus, for example, a package can be a cryocontainer used to contain suitable quantities of peritoneal stem cells and/or peritoneal cells described herein. The packaging material generally has an external label which indicates the contents and/or purpose of the kit and/or its components.

As disclosed herein, the inventors implanted plastic tubing templates into the mouse peritoneum, which were harvested after 8 weeks. The template tubing became covered with tissue and, after the tubing had been carefully removed, the tissue capsules were transplanted into the abdominal aorta of the same mice in which they were grown, as interposition grafts.

As further disclosed herein, high frequency micro-ultrasound image analysis of the tissue capsule grafts demonstrated that they remained patent following grafting. Blood flow analysis measured through the downstream hindlimb revealed no significant differences between tissue grafts and vein or arterial grafts 4 months after transplantation. While the harvested tissue capsules did not express vascular cell markers, the tissue grafts were lined with endothelial-like cells, and the vessel wall cells stained for α-actin, suggesting that tissue capsule cells acquired the phenotype of vascular cells. Thus, the inventors believed that the mouse peritoneum contains a population of primitive cells with a stem/progenitor cell phenotype. For further support, the inventors determined the presence of side population cells and Lin−/Sca-1+/c-kit+ cells within the resident peritoneal population. Approximately 0.10±0.05% (n=6) of total peritoneal cells excluded Hoechst 33342 dye, similar to the level found with bone marrow cells. Flow cytometry analysis showed that 3.6±0.1% (n=6) of peritoneal-derived cells expressed stem cell markers (Lin$^-$/Sca-1$^+$/c-kit$^+$), compared to 1.9±0.2% (n=6) for bone marrow-derived positive control. Furthermore, sex-mismatch competitive repopulation assays and re-transplantation experiments (n=10) showed that the reconstituted bone marrow from the transplanted animals contains a cell population derived from donor cells of peritoneal origin, and these cells have long-term regeneration capabilities. The gene expression profiling revealed that peritoneal cells display a gene expression program that is involved with development and morphogenesis events.

Thus, as disclosed herein, the inventors demonstrate that the mouse peritoneum contains multiple distinct stem cell populations or primitive precursors capable of regenerating bioengineered tissues and reconstituting the hematopoietic system of lethally irradiated mice.

As would be apparent to one of skill in the art, the invention may be practiced using any variety of mechanical substrates and materials for the isolation and use of progenitor/stem cells and is not in any way limited to a plastic tubing template.

In one embodiment, the invention provides a method of isolating progenitor and/or stem cells by implanting a mechanical substrate in a peritoneal cavity. In another embodiment, the isolated progenitor and/or stem cell has characteristics of a hematopoietic stem cell. In another embodiment, the invention provides a method of isolating stem cells from a peritoneal cavity of a mammal. In another embodiment, the mammal is a mouse. In another embodiment, the mammal is a human. In another embodiment, the invention provides a method of transporting stem cells from a peritoneal cavity to another organ. In one embodiment, the isolation and/or transplantation of stem cells provides a method of treatment. In another embodiment, the isolation and/or transplantation of stem cells provides a method of treatment for heart disease and/or vascular disease. In another embodiment, the method of treatment includes the expression of a genetic sequence of interest from a stem cell. In another embodiment, the method of treatment includes the transportation of a stem cell to an organ. In another embodiment, the treatment includes proliferating and/or differentiating a cell in a secondary recipient host, stimulating reperfusion/neovascularization, reconstituting at least partially a hematopoietic system, and/or grafting into an organ.

As disclosed herein, the cells isolated from the peritoneal cavity exhibited markers and characteristics of hematopoietic and embryonic stem cells. As further disclosed herein, stem cell characteristics were demonstrated by cells' ability to promote reperfusion of mouse ischemic hindlimb and engraft into various organs of lethally-irradiated recipient mice, and a gene expression profile on microarray analysis that was primarily related to differentiation, development and morphogenesis. FACS analysis showed that peritoneal cells contain cells with side population characteristics and hematopoietic stem cell attributes.

In one embodiment, the invention provides a method of isolating stem cells from a peritoneal cavity that includes demonstrating stem cell characteristics. In another embodiment, the invention provides a method of isolating a stem cell from a peritoneal cavity that includes demonstrating the cells' ability to promote reperfusion of ischemic hindlimb and engrafting into various organs of lethally-irradiated recipients. In another embodiment, the invention provides a method of isolating a stem cell from a peritoneal cavity that includes demonstrating a gene expression profile on microarray analysis that is primarily related to differentiation, development and morphogenesis. In another embodiment, the invention provides a method of isolating a progenitor/stem cell from a peritoneal cavity that includes FACS analysis showing that peritoneal cells contain cells with side population characteristics.

In another embodiment, the present invention provides methods of isolating a progenitor and/or stem cell, comprising one or more of the following steps: implanting a mechanical substrate into a peritoneum of a mammal; harvesting the implanted mechanical substrate after approximately 8 weeks; removing tissue from the harvested mechanical substrate; and transplanting removed tissue into the abdominal aorta of a mammal as interposition grafts. In another embodiment, the mammal is a mouse. In another embodiment, the mammal is a human.

In another embodiment, the present invention provides methods of isolating a progenitor and/or stem cell, comprising one or more of the following steps: preparing a peritoneal derived graft of a mammal; characterizing stem cell function of a cell from the graft; characterizing stem cell phenotype of a cell from the graft; and characterizing stem cell genotype of a cell from the graft. In another embodiment, methods of isolating progenitor and/or stem cells allow at least partial regeneration of bioengineered tissue and/or reconstitution of a hematopoietic system.

Embodiments of the present invention include methods for isolation of peritoneal stem cells, and methods for generating peritoneal stem cells and cell lines. Additional embodiments of the present invention include methods for using peritoneal stem cells or cell lines for a variety of purposes; for example, to test therapeutic products, to study peritoneal cavity diseases, and to obtain peritoneal cavity stem cell and cell line products.

The present invention is also directed to kits for isolating peritoneal stem cells and hematopoietic and embryonic stem cells; kits for generating peritoneal stem cell lines and hematopoietic and embryonic stem cell lines; and kits for using peritoneal stem cells or cell lines, and hematopoietic and embryonic stem cells or cell lines, to test therapeutic products, to study hematopoietic conditions, and/or to obtain peritoneal derived products.

Each kit is an assemblage of materials or components. The exact nature of the components configured in each inventive kit depends on its intended purpose. For example, some embodiments are configured for the purpose of isolating the peritoneal stem cells and/or cells described herein; generating the peritoneal stem cell lines and/or cell lines described herein; and/or using the peritoneal stem cells and stem cell lines or the cells or cell lines described herein to test therapeutic products. For example, some embodiments are configured for the purpose of stimulating reperfusion/neovascularization, reconstitute the hematopoietic system, graft into various organs, and/or proliferate and differentiate cells in a secondary recipient host. In some embodiments, the kits are configured particularly for mammalian subjects. In another embodiment, the kits are configured particularly for human subjects. In further embodiments, the kits are configured for veterinary animals, such as such as, but not limited to, farm animals, domestic animals, and laboratory animals.

Instructions for use may be included in the kit. "Instructions for use" typically include a tangible expression describing the technique to be employed in using the components of the kit for a desired purpose, such as for isolating the peritoneal stem cells and/or cells described herein, generating the peritoneal stem cell lines and/or cell lines described herein, and/or using the peritoneal stem cells and stem cell lines or the cells or cell lines described herein to test therapeutic products. Other examples of a desired purpose include stimulating reperfusion/neovascularization, reconstitute the hematopoietic system, graft into various organs, and/or proliferate and differentiate cells in a secondary recipient host.

Optionally, the kits also contain other useful components, such as, buffers (e.g., PBS), growth media, tissue culture plates, multiple-well plates, flasks, chamber slides, differentiation media, stem cell media, goat serum, fetal bovine serum, basic fibroblast growth factor, epidermal growth factor, diluents, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s).

One skilled in the art will recognize many methods and materials similar or equivalent to those described herein, which could be used in the practice of the present invention. Indeed, the present invention is in no way limited to the methods and materials described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Isolation of Stem Cells

Polyethylene (PE) tubing was inserted into the peritoneal cavity of mice. Through implantation of foreign bodies in the peritoneal cavity, an inflammatory response is initiated and culminates in the production of a fibrous capsule. The structure was removed after 8 weeks and the tissue was separated from the tubing.

The tissue was autografted into the abdominal aorta of mice. The blood flow was measured by Laser Doppler imaging one month after grafting and the bioengineered grafts were harvested and analyzed by immunohistochemistry.

Example 2

Characterization of Stem Cells

Cells isolated from the peritoneal cavity exhibited markers and characteristics of hematopoietic and embryonic stem cells. Stem cell characteristics was demonstrated by their ability to promote reperfusion of mouse ischemic hindlimb and engraft into various organs of lethally-irradiated recipient mice, and a gene expression profile on microarray analysis that was primarily related to differentiation, development and morphogenesis. FACS analysis showed that peritoneal cells contain cells with side population characteristics and hematopoietic stem cell characteristics.

Example 3

Expression Profiling of Peritoneal Cells Using Microarray Analysis

Peritoneal cells were isolated from MRL, BALB/c, and C57BL/6 mice. Inventors then isolated RNA and performed in vitro RNA amplification. Inventors then performed affymetrix oligonucleotide array hybridization with mouse MOE-430 (22,000 probes). Inventors then performed gene expression analysis using Affymetrix Microarray analysis Suite 4.0, Presence/Absence calls. Inventors then performed bioinformatics analysis; specifically, database searches, Genbank, GO, Unigene, OMIM, and PubMed were used for the analysis. Inventors then performed a functional annotation; specifically, protein classification and putative functions.

Example 4

Tissue Engineered Graft Grown in the Mouse Peritoneal Cavity: the Role of Peritoneal-derived Stem/Progenitor Cells The inventors generated bioengineered blood vessels in mouse peritoneal cavity, showing that the mouse peritoneum contains primitive cells with regenerative potential.

The inventors implanted plastic tubing templates into the mouse peritoneum, which were harvested after 8 weeks. The template tubing became covered with tissue and, after the tubing had been carefully removed, the tissue capsules were transplanted into the abdominal aorta of the same mice in which they were grown, as interposition grafts.

High frequency micro-ultrasound image analysis of the tissue capsule grafts demonstrated that they remained patent following grafting. Blood flow analysis measured through the downstream hindlimb, revealed no significant differences between tissue grafts and vein or arterial grafts 4 months after transplantation. While the harvested tissue capsules did not express vascular cell markers, the tissue grafts were lined with endothelial-like cells, and the vessel wall cells stained for α-actin, suggesting that tissue capsule cells acquired phenotype of vascular cells. Thus, the inventors believed that the mouse peritoneum contains a population of primitive cells with a stem/progenitor cell phenotype. For further support, the inventors determined the presence of side population cells and Lin−/Sca-1+/c-kit+ cells within the resident peritoneal population. Approximately 0.10±0.05% (n=6) of total peritoneal cells excluded Hoechst 33342 dye, similar to the level found with bone marrow cells. Flow cytometry analysis showed that 3.6±0.1% (n=6) of peritoneal-derived cells expressed stem cell markers (Lin$^-$/Sca-1$^+$/c-kit$^+$), compared to 1.9±0.2% (n=6) for bone marrow-derived positive control. Furthermore, sex-mismatch competitive repopulation assays and re-transplantation experiments (n=10) showed that the reconstituted bone marrow from the transplanted animals contains a cell population derived from donor cells of peritoneal origin, and these cells have long-term regeneration capabilities. The gene expression profiling revealed that peritoneal cells display a gene expression program that is involved with development and morphogenesis events.

Thus, the mouse peritoneum contains multiple distinct stem cell populations or primitive precursors capable of regenerating bioengineered tissues and reconstituting the hematopoietic system of lethally irradiated mice.

Example 5

Tissue Capsules After Harvest

Following the harvest of the implant, the tissue capsules that formed around the tubing was carefully separated by cutting one end and gently sliding it off the tube. It was then washed and immersed in a heparinized saline solution (100 units/ml.) prior to transplantation. The functionality of tissue capsules is determined by grafting the newly formed tissue into the abdominal aorta of the same mice to generate an auto-graft. The functionality of the auto-graft to promote blood flow was compared to two positive control groups, receiving either venous or arterial grafts. In the venous iso-graft group, a segment of the inferior vena cava was harvested from donor mice, and grafted into the abdominal aorta of the recipient mice, using the same surgical procedure used to transplant the capsule graft. The same procedure was followed for the arterial iso-graft group, except a segment of the thoracic aorta was harvested from donor mice and grafted into the abdominal aorta of the recipient mice. For the negative control group, the abdominal aorta was simply occluded by a double ligation with 9-0 silk. The grafts were harvested at either 4 or 16 weeks after implantation.

The inventors used an abdominal grafting site to monitor the functionality of auto-grafts, allowing them to readily monitor the physical activity of mice as an indication of graft patency. In the negative control group where the abdominal artery was occluded by ligation, the mice lost their ability to move shortly after surgery and they had to be euthanized; whereas, all the surviving mice receiving the capsule grafts remained vigorous, suggesting good blood flow into the lower extremities.

Example 6

Patency and Cellular Composition of the Capsule Grafts

The inventors used three methodologies to assess patency of grafts: the physical activity of the mice, micro-ultrasound and Laser Doppler imaging. The graft was considered successful if it met the following criteria: at the time of implantation and harvesting it was strongly pulsating and fully distended, the animal had normal motor activity, and the graft was patent as indicated by a good blood flow through the graft, as well as through the bilateral femoral arteries. In addition, subsequent immunostaining examination of the sections showed no evidence of clot formation. Conversely, grafts that were not patent were flaccid, retracted and had no detectable pulsation. Microscopically, they clearly showed a clot in their lumen. Using these criteria, mice with successful grafts were retained for investigations.

The inventors used high frequency micro-ultrasound to determine the patency of the abdominal grafts using the Vevo 770 (VisualSonics; Toronto, Canada) micro-imaging system, with the RMV 706 scan head at a center frequency of 30 MHz and 10% power. This system provided a lateral resolution of 100 μm and an axial resolution of 40 μm. The mice were imaged at a frame rate of 30 fps.

To further determine functionality of the capsule graft, the inventors measured blood flow into bilateral femoral artery by laser Doppler imaging (LDI). As compared to baseline values, the average blood flow in the capsule graft and in the vein graft recipient groups one day after surgery, decreased by 40% (2.19±0.13 vs. (1.29±0.24) and 35% (2.21±0.01 vs. 1.43±0.27), respectively. In contrast, there was no significant difference measured in the blood flow of mice that received arterial grafts (2.2±0.09 vs. 1.79±0.1). Subsequently, there was no difference in blood flow between mice with successful grafts at 4 weeks or at 16 weeks after grafting. This shows that remodeling of both capsule grafts and venous grafts were largely completed at 4 weeks post-implantation and acquire a phenotype similar to that of arterial grafts. It is well documented that venous grafts undergo arterialization, i.e., their media expand by increasing the number of smooth muscle cells. It is, therefore, possible that a similar mechanism operates in the remodeling of capsule grafts, and that peritoneal-derived stem/progenitor cells in part contribute to the remodeling of capsule grafts.

Immunohistological analysis of the capsule auto-grafts harvested 4 weeks after grafting into abdominal aorta of C57BL/6, BALB/c and MRL mice revealed the thickness of the capsule grafts increased compared to the freshly harvested capsule, i.e., the grafts have been arterialized. While cells in the harvested tissue capsule did not express markers of smooth muscle cell or endothelial cells, the capsule graft cells expressed these markers. Anti smooth muscle α-actin antibody strongly stained the cells in the vessel wall of capsule grafts, similar to the positive control vein graft. Anti-CD31 staining showed that endothelial cells lined the lumen of the capsule grafts. Anti-MOMA-2 antibody stained few macrophages, if any, in the capsule grafts. To determine whether stem/progenitor cells that were detected in the freshly harvested tissue capsule are present in the capsule grafts, sections were stained with anti-Sca-1 antibody. Immunostaining showed that some cells in the lumen and capsule wall of the grafts contain stem cell. Collectively, these results show that the tissue capsule undergoes arterialization when exposed to arterial pressure, possibly in response to pulsatile flow, and the primitive cells contribute to this remodeling.

Example 7

Phenotype of the Peritoneal Cells

The inventors investigated the source of endothelial-like and smooth muscle-like cells in the peritoneal-derived grafts. The endothelial cells in the grafts are thought to be in part originated from the donor graft (Sata, M., Saiura, A., Kunisato, A., Tojo, A., Okada, S., Tokuhisa, T., Hirai, H., Makuuchi, M., Hirata, Y., and Nagai, R. 2002 *Nat Med* 8:403-409; Shimizu, K., Sugiyama, S., Aikawa, M., Fukumoto, Y., Rabkin, E., Libby, P., and Mitchell, R. N. 2001. Host bone-marrow cells are a source of donor intimal smooth-muscle-like cells in murine aortic transplant arteriopathy. *Nat Med* 7:738-741). The smooth muscle cells on the other hand are believed to exclusively originate from the donor tissues (Bentzon, J. F., Weile, C., Sondergaard, C. S., Hindkjaer, J., Kassem, M., and Falk, E. 2006 *Arterioscler Thromb Vasc Biol* 26:2696-2702; De Palma, M., Venneri, M. A., Roca, C., and Naldini, L. 2003 *Nat Med* 9:789-795; Voswinckel, R., Ziegelhoeffer, T., Heil, M., Kostin, S., Breier, G., Mehling, T., Haberberger, R., Clauss, M., Gaumann, A., Schaper, W., et al. 2003 *Circ Res* 93:372-379; Ziegelhoeffer, T., Fernandez, B., Kostin, S., Heil, M., Voswinckel, R., Helisch, A., and Schaper, W. 2004 *Circ Res* 94:230-238). Since the tissue capsules did not express smooth muscle cell markers and the markers appeared only after grafting, it was possible that the tissue capsule cells derived from mouse peritoneum contains a population of cells that the express markers of vascular cells, in response to environmental cues (arterial pressure). This event could contribute to the arterialization of tissue capsule grafts.

As the smooth muscle cells present within the graft appeared to originate exclusively from donor tissue, the inventors reasoned the mouse peritoneum might contain primitive cell populations, capable of expressing a vascular cell phenotype in response to environmental cues. To explore this, the inventors used multiple approaches—global gene expression profiling, candidate transcription factor expression, side population analysis, cell-surface marker studies, long-term competitive repopulation investigation, and ischemic hindlimb reperfusion studies—to gain an insight into the role of peritoneal cells in the generation of tissue.

Example 8

Phenotype of the Peritoneal Cells: Transcriptional Profiling of Tissue Capsule Cells and Mouse Peritoneal Cells To determine the nature of cells that contribute to the formation of tissue capsule in mouse peritoneum, the inventors determined expression profile of freshly-harvested tissue capsules isolated from 3 strains of mice. As the activity of tissue capsule and capsule grafts were similar among the 3 strains of mice, the inventors reasoned that tissue capsules as well as peritoneal cells isolated from C57BL/6, BALB/c, and MRL mice share transcriptome signatures, and that this shared gene expression program is likely responsible for the generation of tissue in mouse peritoneum. To test this hypothesis, total RNA was extracted from the tissue capsules isolated from the 3 strains of mice (3 tissue capsules/mouse strain). In addition, 5 mls of saline was injected into mouse peritoneum, and the resulting peritoneal wash was harvested (about 3 ml), centrifuged to isolate peritoneal cells, and total RNA was extracted. Approximately $1 \times 10^6$ peritoneal cells/mouse are routinely isolated. The transcription profile of the tissue capsule cells and peritoneal cells were determined by microarray analysis.

Total RNA was purified with the RNeasy mini kit (Qiagen) after isolation with TRIzol reagent (Invitrogen) according to the manufacturer's instructions. RNA was resuspended in DEPC treated distilled water and further purified using RNA Tack™ Resin (Ultraspec™-II RNA Isolation System, Biotecx) according to the manufacturer's instructions. After purification, an aliquot of total RNA was electrophoresed (2.0% agarose gel) and visualized by staining with ethidium bromide to confirm the absence of significant degradation. First strand cDNA was synthesized from 5 μg of total RNA from each sample in the presence of Cy5 or Cy3 dCTP, respectively. Aliquots (200 μl) of the mixture were hybridized onto Affymetrix GeneChip Mouse Expression Microarray MOE-430 (~22,000 cDNA and ESTs) according to Affymetrix's instructions using a GeneChip Hybridization Oven 640 (Affymetrix). The microarray analysis was performed in Microarray Core Facility at Cedars-Sinai Medical Center.

Example 9

Phenotype of the Peritoneal Cells: Transcriptional Profiling of Tissue Capsule Cells and Mouse Peritoneal Cells—Data Processing Image acquisition of the mouse oligo microarrays was performed on an Agilent G2565AA Microarray Scanner System, and feature extraction was performed with Agilent feature extraction software (version A.6.1.1, Agilent Technologies). Normalization was carried out using a LOWESS algorithm. Dye-normalized signals of Cy3 and Cy5 channels were used in calculating log ratios. Features with a reference value of <2.5 standard deviations for the negative control were regarded as missing values. Those features with values in at least two-thirds of the experiments and present in at least one of the replicates were retained for further analysis. Reproducibility of microarray results, as measured by the variation between arrays for signal intensities, was assessed using box plots (GeneData). Heat maps were generated using HeatMap Builder software.

To identify differentially expressed transcripts, pairwise comparison analysis was carried out with a Data Mining Tool 3.0 (Affymetrix). This analysis compares the differences in values of perfect match to mismatch of each probe pair in the base-line array to its matching probe on the experimental array. P values were determined by the Wilcoxon's signed rank test and denoted as an increase, a decrease, or no change. Analysis also provides the signal log ratio, which estimates the magnitude and direction of change of a transcript when two arrays are compared. The signal ratio output was converted into fold change as recommended by Affymetrix.

Example 10

Phenotype of the Peritoneal Cells: Transcriptional Profiling of Tissue Capsule Cells and Mouse Peritoneal Cells—Genetic Characterization of Peritoneal Cells Since tissue capsule formation and capsule grafts in C57BL/6, BALB/c, and MRL strains of mice exhibited a similar phenotype, the inventors reasoned that this phenotype is determined by a gene expression program that is shared among the peritoneal cells from the 3 strains of mice. Genes enriched in tissue capsule cells or in peritoneal cells were assigned to functional categories using NetAffx.com and National Center for Biotechnology Information (NCBI) databases. Gene lists were intersected by Unigene number and by Gene Ontology (GO) to determine overlaps and the function of highly expressed genes. Functionally annotated data were organized into fully searchable spreadsheets; all raw data are also included in the appendix.

In addition to identifying strain-specific genes, the data showed that there was a subset of genes commonly enriched in all tissue capsules isolated from the 3 strains of mice. Similar results were obtained when expression profiles of peritoneal cells from the 3 strains of mice were compared. The probability of observing such an overlap by chance as estimated using hypergeometrical distribution is extremely low ($P=10^{-11}$). The data demonstrates that the vast majority of genes found in the tissue capsule from the 3 strains of mice overlap, showing that the peritoneal cells from the 3 strains are very similar to one another. These genes likely represent the conserved molecular components expressed in peritoneal cells. This global overlap explains the observations that the tissue capsule generated in the peritoneal cavity of the 3 strains of mice exhibited similar characteristics and functional activity before and after implantation into abdominal aorta.

The inventors defined a genome-wide transcriptional profile of tissue capsule cells and peritoneal cells by comparing 3 distinct sets of genes that are up-regulated in cells isolated from C57BL/6, BALB/c, and MRL mice. The distribution of genes within the shared transcriptome across functional categories is shown herein. Molecules thought to be involved in development, morphogenesis, and differentiation tend to be overrepresented in the tissue capsule cells.

Example 11

Phenotype of the Peritoneal Cells: Expression of Key Transcription Factors by the Peritoneal Cells Elements that regulate the phenotype of stem/progenitor cells are transcription factors, chiefly among them are Oct-4, Nanog, Sox2, and Rex-1. Oct-4 is a transcription factor belonging to the class V of POU factors, which are enriched in mouse embryonic cells. Oct-4 and another homeodomain transcription factor, Nanog, are among the functionally characterized genes that are crucial to the mouse embryonic cell molecular signature. In the absence of Oct-4, the stem cells trans-differentiate into trophectodermal cells (Nichols, J., Zevnik, B., Anastassiadis, K., Niwa, H., Klewe-Nebenius, D., Chambers, I., Scholer, H., and Smith, A. 1998 Cell 95:379-391), whereas loss of Nanog results in an increase in extra-embryonic endodermal transcripts (Mitsui, K., Tokuzawa, Y., Itoh, H., Segawa, K., Murakami, M., Takahashi, K., Maruyama, M., Maeda, M., and Yamanaka, S. 2003 Cell 113:631-642). Overexpression of Nanog allows mouse embryonic cells growth in the absence of leukemia inhibitory factor (Chambers, I., Colby, D., Robertson, M., Nichols, J., Lee, S., Tweedie, S., and Smith, A. 2003 Cell 113:643-655), a factor that is required for the maintenance of the stem cell lines, whereas overexpression of Oct-4 induces the differentiation of mouse embryonic stem cells into endoderm and mesoderm. When Oct-4 forms a complex with the transcription factor Sox2, it up-regulates its own expression as well as the expression of Rex-1 and Nanog, this interaction identifies Oct-4 as a key regulator of embryonic stem cells genes.

The inventors found that these stem cell-specific transcription factors are highly expressed among the overlap genes described herein. Therefore, they used RT-PCR to establish the expression of Oct-4, Nanog, Sox2, and Rex-1 transcription factors in the tissue capsule cells isolated from capsules grown in peritoneal cavity of C57BL/6, BALB/c, and MRL mice. RT-PCR analysis of total RNA confirmed the expression pattern of these transcription factors. These transcription factors were not expressed in the negative control aortic smooth muscle cells isolated from the 3 strains of mice studied. The data further confirms the results of comparative global gene expression studies and further demonstrates that capsule cells have characteristics of stem/progenitor cells, further confirming the results of immunostaining experiments described herein.

The immunostaining, expression profiling, and RT-PCR studies demonstrate that the cellular components of tissue capsules, grown in the peritoneal cavity of the three strains of mice examined, display characteristics of stem cells. The mouse peritoneum contains stem cells that can contribute to the generation of tissue capsules. To explore this, they examined the ability of cells present in the mouse peritoneum to exclude Hoechst dye (side population cells) and to express stem cell-specific antigens.

Example 12

Phenotype of the Peritoneal Cells: Expression of Key Transcription Factors by the Peritoneal Cells—Side Population Cells Hoechst side population analysis is a critical technique for detecting stem cells and early progenitors. Many types of adult stem cells from a variety of tissues, such as bone marrow, muscle, neurosphere, and testis, can be enriched as 'side population' cells based on their ability to efflux the fluorescent dye Hoechst 33342, owing to the expression of the ATP binding assette transporter, ABCG2 (Challen, G. A., and Little, M. H. 2006 *Stem Cells* 24:3-12).

The inventors have determined whether peritoneal cells isolated from C57BL/6 mice have characteristics of side population cells. To establish this, peritoneal cells were treated with Hoechst 33342 and then analyzed by FACS. Bone marrow cells were used as a positive control. The side population appeared as the 'Hoechst low fraction' capable of pumping out the dye and represents 0.05%-0.10% of viable cells from peritoneal cells and bone marrow. The non-side population cells that retain high levels of Hoechst staining, the main population of cells, represented the vast majority of cells present. They harvested approximately $1\times10^6$ peritoneal cells from each stain of mice, of which $0.5\times10^3$-$1\times10^3$ were side population cells.

To determine the specificity of dye uptake, cells were treated with Hoechst in the presence of verapamil, an inhibitor of the ABCG2 transporter, which prevents effluxing the dye. The treatment with verapamil abalated side population cells in both peritoneal cells and bone marrow cells. The data shows that the peritoneal cells are heterogeneous and contain a subpopulation of cells, which possess the characteristics of stem/progenitor cells.

Example 13

Phenotype of the Peritoneal Cells: Expression of Key Transcription Factors by the Peritoneal Cells—Expression of Stem Cell-Specific Cell-Surface Marker The inventors further confirmed the result of side population studies by investigating the expression of cell-surface markers that characterize stem cells. The Sca-1 and c-kit cell surface antigens are widely used to identify and isolate hematopoietic stem cells using monoclonal antibodies and flow cytometry. They used a similar strategy to determine whether peritoneal cells isolated from C57BL/6 mice express these cell surface markers. Bone marrow cells isolated from the same mice that were used for preparation of peritoneal cells were used as a positive control. Freshly isolated cells were stained with biotinylated lineage-specific antibodies (Mouse Lineage Panel, containing anti-CD45R, anti-CD11b, anti-TER119, anti-Gr-1, and anti-CD3e (BD Pharmingen)), fluorescein isothiocyanate (FITC)-anti-Sca-1, and allophycocyanin (APC)-anti-c-kit (BD Pharmingen). Cells were analyzed using the FACS Calibur (Becton, Dickinson and Company) at the Cedars-Sinai Flow Cytometry Core Facility.

When compared to total cells, the percentage of lineage negative/Sca-1 positive cells in the peritoneal cells (PC) and bone marrow cells (BM) are 4±1% and 4.7±2.3%, respectively. When the expression of both Sca-1 and c-kit antigens were measured, the number of positive cells was decreased, 1.6±0.1% for PC cells and 1.9±0.2% for BM cells. It appears that the number of $Lin^-/Sca-1^+/c-kit^+$ in peritoneal cells is comparable to those in the positive control bone marrow cells. These results confirm the side population studies and show that the peritoneal cells are heterogeneous and there is a subpopulation of cells with a stem cell phenotype. We can isolate approximately $1\times10^3$-$5\times10^3$ $Lin^-/Sca-1^+/c-kit^+$ from freshly isolated peritoneal cells from each stain of mice. Generally, the MRL stain produced 20±10% more LSK cells than C57BL/6 or BALB/c mouse strains.

Example 14

Phenotype of the Peritoneal Cells: Expression of Key Transcription Factors by the Peritoneal Cells—Functional Activity of Peritoneal Cells The results of the comparative global gene expression studies, expression of stem cell-specific transcription factor, analysis of side population cells, and studies of cell-surface markers strongly show that peritoneal cells isolated from the 3 strains of mice have stem/progenitor cell characteristics. To determine the functional activity of these cells, the inventors used two widely established assays: stimulating re-perfusion of ischemic tissue and reconstituting hematopoietic system of lethally irradiated mice.

Example 15

Phenotype of the Peritoneal Cells: Expression of Key Transcription Factors by the Peritoneal Cells—Peritoneal Cells Promote Neovascularization of Ischemic Tissue Past studies have shown the ability of side population cells (Goodell, M. A., Jackson, K. A., Majka, S. M., Mi, T., Wang, H., Pocius, J., Hartley, C. J., Majesky, M. W., Entman, M. L., Michael, L. H., et al. 2001 *Ann N Y Acad Sci* 938:208-218, discussion 218-220; Jackson, K. A., Majka, S. M., Wang, H., Pocius, J., Hartley, C. J., Majesky, M. W., Entman, M. L., Michael, L. H., Hirschi, K. K., and Goodell, M. A. 2001 *J Clin Invest* 107:1395-1402) and bone marrow-derived multipotent adult progenitor cells (Jiang, Y., Vaessen, B., Lenvik, T., Blackstad, M., Reyes, M., and Verfaillie, C. M. 2002 *Exp Hematol* 30:896-904; Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., et al. 2002 *Nature* 418:41-49) to differentiate into endothelial cells. Additionally, local intramuscular autologous bone marrow cell therapy (Hamano, K., Li, T.-S., Kobayashi, T., Tanaka, N., Kobayashi, S., Matsuzaki, M., and Esato, K. 2001 *Surgery* 130:44-54; Shintani, S., Murohara, T., Ikeda, H., Ueno, T., Sasaki, K.-i., Duan, J., and Imaizumi, T. 2001 *Circulation* 103:897-903; Iwase, T., Nagaya, N., Fujii, T., Itoh, T., Ishibashi-Ueda, H., Yamagishi, M., Miyatake, K., Matsumoto, T., Kitamura, S., and Kangawa, K. 2005 *Circulation* 111:356-362) or adipose tissue-derived stem cells (Miranville, A., Heeschen, C., Sengenes, C., Curat, C. A., Busse, R., and Bouloumie, A. 2004 *Circulation* 110:349-355) have been demonstrated to induce therapeutic angiogenesis in experimental ischemic limb models. Since peritoneal cells exhibit the characteristics of stem/progenitor cells, the inventors asked whether these cells could improve neovascularization of ischemic tissue. To explore this, peritoneal cells were harvested from BALB/c mice and injected into ischemic hindlimb of the same strain of mice, essentially as previously described (Sharifi, B. G., Zeng, Z., Wang, L., Song, L., Chen, H., Qin, M., Sierra-Honigmann, M. R., Wachsmann-Hogiu, S., and Shah, P. K. 2006 *Arterioscler Thromb Vasc Biol* 26:1273-1280). Briefly, the left femoral artery was ligated at its proximal origin from the iliac artery and distally at the bifurcation into the popliteal and saphenous arteries. The unligated right contralateral artery was used as a control. Peritoneal cells were injected into ischemic hindlimb and blood flow in the ischemic and normal limbs was measured after the indicated times by a Laser Doppler Imaging System. As bone marrow cells promote blood flow into ischemic hindlimb, these cells were used as a positive control. The BALB/c mice were chosen for these experiments because they have low level of spontaneous collateral growth formation in the ischemic hindlimb (Helisch, A., Wagner, S., Khan, N., Drinane, M., Wolfram, S., Heil, M., Ziegelhoeffer, T., Brandt, U., Pearlman, J. D., Swartz, H. M., et al. *Arterioscler Thromb Vasc Biol* 26:520-526).

A representative Laser Doppler Image (LDPI) of the ischemic and non-ischemic limb is shown herein. The data clearly shows that the injection of peritoneal cells stimulated blood flow in the ischemic hindlimb similar to those of positive control bone marrow cells. Cumulative LDPI analysis of mice injected with peritoneal cells showed that the blood flow increased by $52\pm1\%$ at day 4, $68\pm1\%$ at day 7, $50\pm1.2\%$ at day 14, and $37.5\pm1.3\%$ at day 21 post surgeries compared to control group. This level of increase in the blood flow is almost identical to those of positive control bone marrow cells. The data was corroborated by histological analysis revealing an increase in capillary density in muscle from recipient of peritoneal-derived cells compared to control mice, similar to those of recipient of bone marrow cells. The data shows that, like bone marrow cells, peritoneal-derived cells significantly stimulated angiogenesis in ischemic tissue to an almost identical extent as that of positive control bone marrow cells.

Example 16

Phenotype of the Peritoneal Cells: Expression of Key Transcription Factors by the Peritoneal Cells—Peritoneal Cells Reconstitute Hematopoietic System of Lethally Irradiated Mice The characterization of peritoneal cells as stem/progenitor cells prompted the inventors to ask whether peritoneal cells are capable of repopulating hematopoietic system of lethally irradiated mice. The definitive experiment to address this issue is the long-term repopulation assay. A theory behind this assay is that stem cells, which give rise to multilineage hematopoiesis in primary recipients, are also capable of repeating this process in recipients of secondary transplants (Harrison, D. E. 1980 *Blood* 55:77-81; Harrison, D. E., Jordan, C. T., Zhong, R. K., and Astle, C. M. 1993 *Exp Hematol* 21:206-219). In this assay, donor cells (usually, from a male donor), containing an unknown frequency of stem cells, are co-transplanted with a standard number of helper normal bone marrow cells from female mice. This latter population provides radio-protective support cells that quickly produce the mature cells necessary to ensure survival of mice. This function is particularly important during the initial 6 weeks that it takes for the donor stem cells to develop into a sufficient number of mature hematopoietic cells. The drawback of this assay is the duration of study, which usually requires 3-6 months to complete. This long period is necessary to ensure that the short-lived progenitors are exhausted and replaced by progeny of the transplanted stem cells.

Competitive repopulation using the sex-mismatch system was performed essentially as described previously (Wang, L., Sharifi, B. G., Pan, T., Song, L., Yukht, A., and Shah, P. K. *J Am Coll Cardiol* 48:1459-1468) Briefly, $1\times10^6$ freshly isolated peritoneal cells from male C57BL/6, BALB/c, or MRL mice were mixed with $2\times10^5$ bone marrow competitor cells from isogenic female mice and then transplanted into lethally irradiated female isogenic mice (10 mice/group). The animals were euthanized after 4 months, and their organs, including bone marrow and peripheral blood were collected. Genomic DNA was isolated from white blood cells for the analysis of Y-chromosome by PCR, essentially as described previously (Wang, L., Sharifi, B. G., Pan, T., Song, L., Yukht, A., and Shah, P. K. 2006 *J Am Coll Cardiol* 48:1459-1468). PCR analysis of genomic DNA isolated from the white blood cells of the recipient mice showed that all 10 recipient mice were positive for Y-chromosome. These results show that peritoneal cells contributed to the long-term reconstitution of the hematopoietic system of primary recipient mice. Further, this shows that the peritoneal cells must have homed into their niches in the supportive bone marrow microenvironment, grafted, and matured before being released into the circulation of the primary recipient mice.

Example 17

Phenotype of the Peritoneal Cells: Expression of Key Transcription Factors by the Peritoneal Cells—Peritoneal Cells Engraft to Various Organs The inventors also asked whether Y-chromosome could be detected in the organ of primary recipient mice, in addition to peripheral blood. PCR analysis of genomic DNA isolated from various organs of recipient mice found Y-chromosome in bone marrow, brain, heart, kidney, liver, lung, spleen, and white blood cells, as shown herein. The chromosome isolated from negative control female mice and positive control male mice is also shown herein. The β-globin was used as a loading control. The data shows that engraftment occurred in the various organs of all 10 recipient mice transplanted with the peritoneal cells.

Example 18

Phenotype of the Peritoneal Cells: Expression of Key Transcription Factors by the Peritoneal Cells—Peritoneal Derived Cells Proliferate and Differentiate in the Secondary Recipient Host A major tenet of stem cell biology is that true stem cells must be highly proliferative and able to generate progeny that can repopulate secondary recipients, although this property has well established limits (Jones, R. J., Celano, P., Sharkis, S. J., and Sensenbrenner, L. L. 1989 *Blood* 73:397-401; Mauch, P., and Hellman, S. 1989 *Blood* 74:872-875). The presence of a cell population with stem/progenitor cell phenotype within the peritoneal-derived cell population, specially one which expresses Lin$^-$/Sca-1$^+$/c-kit$^+$ hematopoietic stem cell antigens, prompted the inventors to ask whether these cells display activities similar to those of stem/progenitor cells derived from bone marrow, such as long-term engraftment.

The bone marrow harvested 4 months after the primary transplantation was used for secondary transplantation. The bone marrow cells were harvested from the primary donor mice and 5×10⁶ cells/mouse were transplanted into lethally irradiated isogenic secondary female recipient mouse, essentially as described above (10 mice/group). The radiation control group was not transplanted with bone marrow cells (5 mice/group). All radiation control group of mice died within 10-14 days after irradiation. All the test groups of mice have survived. After 4 months of secondary transplantation, the peripheral blood was collected by retro-orbital bleeding from 3 recipient mice that were originally transplanted with male peritoneal-derived cells (primary transplant) and 3 recipient mice that were originally transplanted with male bone marrow cells (primary transplant, positive control). The PCR analysis of the collected blood from 3 peritoneal-derived recipient mice and 3 bone marrow recipient mice shows the presence of Y-chromosome in all mice groups. The female bone marrow was used as a negative control. β-globin was the control for the peritoneal-derived cells and bone marrow derived cells. The data shows that the bone marrow of the transplanted animals contains a population from the donor cells of peritoneal-derived origin, and may indicate that a hematopoietic stem cell compartment may arise from peritoneal-derived cells. The data shows that mouse peritoneum contain stem progenitor cells with stem cell characteristics, i.e., they proliferate and differentiate into other cell types, such as hematopoietic cells. These cells contribute to the formation of tissue capsule in the mouse peritoneum.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive.

What is claimed is:

1. A method of generating a capsule graft, comprising:
    implanting a mechanical substrate in a peritoneum of a mammal; and
    harvesting the capsule graft from said mechanical substrate, wherein the capsule graft comprises hematopoietic stem cells, and wherein said harvesting occurs at least 8 weeks after implanting said mechanical substrate in the peritoneum.
2. The method of claim 1, wherein the hematopoietic stem cells are Lin⁻/Sca-1⁺/c-kit⁺ hematopoietic stem cells.
3. The method of claim 1, wherein the hematopoietic stem cells stimulate neovascularization when grafted to an organ, vessel or tissue.
4. A method of isolating a population of long-term repopulating hematopoietic stem cells, comprising:
    implanting a mechanical substrate in a peritoneum of a mammal;
    harvesting cells from said mechanical substrate; and
    purifying a population of Lin⁻/Sca-1⁺/c-kit⁺ hematopoietic stem cells.
5. The method of claim 4, wherein the hematopoietic stem cells stimulate neovascularization when grafted to an organ, vessel or tissue.
6. The method of claim 5, wherein said organ, vessel or tissue is an aorta.
7. The method of claim 4, wherein mammal is a mouse.
8. The method of claim 4, wherein mammal is a human.
9. The method of claim 4, wherein the hematopoietic stem cells are capable of at least partially reconstituting the hematopoietic system of a mammal when grafted to an organ, vessel or tissue.

* * * * *

UNITED STATES PATENT AND TRADEMARK OFFICE
CERTIFICATE OF CORRECTION

PATENT NO.       : 8,465,976 B2  
APPLICATION NO.  : 12/526661  
DATED            : June 18, 2013  
INVENTOR(S)      : Sharifi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 356 days.

Signed and Sealed this
Eighth Day of September, 2015

Michelle K. Lee
*Director of the United States Patent and Trademark Office*